United States Patent

Burton et al.

[11] Patent Number: 4,684,639
[45] Date of Patent: Aug. 4, 1987

[54] ANTIBACTERIAL PENICILLINS AND CEPHALOSPORINS

[75] Inventors: George Burton, Carshalton; Desmond J. Best, Southwater, both of England

[73] Assignee: Beecham Group, England

[21] Appl. No.: 627,772

[22] Filed: Jul. 5, 1984

[30] Foreign Application Priority Data

Jul. 7, 1983 [GB] United Kingdom ............ 8318374
Jan. 19, 1984 [GB] United Kingdom ............ 8401443

[51] Int. Cl.$^4$ .............. A61K 31/43; A61K 31/495; A61K 31/545; C07D 499/50; C07D 499/54; C07D 501/24

[52] U.S. Cl. .............. 514/194; 514/201; 540/221; 540/224; 540/225; 540/226; 540/227; 540/228; 540/328; 540/331; 544/90; 544/92; 544/390; 546/121; 560/20; 560/21; 560/39; 560/41; 562/444

[58] Field of Search .............. 260/239.1; 544/22, 26, 544/28, 90, 92, 390; 424/246, 271; 562/444; 560/20, 21, 39, 41; 514/194, 201; 540/221, 224, 225, 226, 227, 228, 328, 331; 546/121

[56] References Cited

U.S. PATENT DOCUMENTS

| | | | |
|---|---|---|---|
| 3,489,751 | 1/1970 | Crast | 544/30 |
| 3,860,631 | 1/1975 | Gleason et al. | 562/439 |
| 4,206,116 | 6/1980 | Naito et al. | 260/239.1 |
| 4,349,551 | 9/1982 | Bentley et al. | 424/250 |
| 4,416,883 | 11/1983 | Bentley | 424/250 |
| 4,447,422 | 5/1984 | Taylor et al. | 424/229 |
| 4,454,128 | 6/1984 | Wetzel et al. | 424/229 |
| 4,539,149 | 9/1985 | Milner | 260/239.1 |

FOREIGN PATENT DOCUMENTS

| | | |
|---|---|---|
| 0071395 | 2/1983 | European Pat. Off. |
| 71554 | 6/1975 | Luxembourg . |
| 1472174 | 5/1977 | United Kingdom . |

Primary Examiner—Werren B. Lone
Assistant Examiner—Vera C. Clarke
Attorney, Agent, or Firm—Jacobs & Jacobs

[57] ABSTRACT

A compound having the partial structure (I)

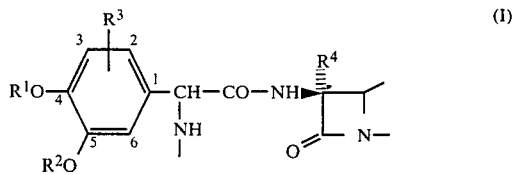

wherein $R^1$ and $R^2$ may be the same or different and each is hydrogen or a group —$COR^5$ or —CO—$OR^5$ wherein $R^5$ represents an optionally substituted hydrocarbon group; $R^3$ is halogen and $R^4$ is hydrogen, methoxy, hydroxymethyl or formamido.

These compounds are suitably bicyclic β-lactam antibiotics.

31 Claims, No Drawings

ANTIBACTERIAL PENICILLINS AND CEPHALOSPORINS

This invention relates to novel β-lactam containing compounds, their preparation and their use, and in particular to a novel class of phenylglycine derivative. These compounds have antibacterial properties, and therefore are of use in the treatment of bacterial infections in humans and animals caused by a wide range of organisms.

Accordingly the present invention provides a class of β-lactam antibiotic having partial structure (I):

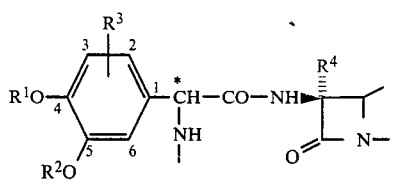
(I)

wherein $R^1$ and $R^2$ may be the same or different and each is hydrogen or a group $—COR^5$ or $—CO—OR^5$ wherein $R^5$ represents an optionally substituted hydrocarbon group;
$R^3$ is halogen and $R^4$ is hydrogen, methoxy or formamido.

Suitably the β-lactam is a bicyclic β-lactam antibiotic.

Suitably $R^1$ and $R^2$ are the same and represent hydrogen or $—COR^5$.

Preferably $R^1$ and $R^2$ are the same and represent hydrogen.

The term halogen used herein refers to fluorine chlorine, bromine and iodine.

Suitably $R^3$ is attached to carbon atom numbered 2 or 3, preferably 2.
Suitable $R^3$ is chlorine, bromine or fluorine
Preferably $R^3$ is chlorine.
Suitably $R^4$ is formamido.
Preferable $R^5$ is $C_{1-6}$ alkyl; in particular methyl.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)-alkyl, aryl, and aryl($C_{1-6}$)alkyl.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl, $C_{1-6}$ alkylcarbonyloxy, or $C_{1-6}$ alkylcarbonyl groups.

Suitable optional substituents for the hydro-carbon groups include $C_{1-6}$ alkyl, heterocyclic, amino, $C_{1-6}$ alkanoyl-amino, mono and di- ($C_{1-6}$) alkylamino, hydroxy, $C_{1-6}$ alkoxy, mercapto, $C_{1-6}$ alkylthio, heterocyclyl-thio, arylthio, sulphamoyl, carbamoyl, amidino, guanidino, nitro, chloro, bromo, fluoro, carboxy and salts and esters thereof, $C_{1-6}$ alkanoyloxy, aryl-carbonyl and heterocyclylcarbonyl.

The carbon atom marked * in formula (I) is asymmetric and the compound may be derived from the side-chain having a D, L or DL configuration at that position. All forms of compound (I) are included in this invention. Suitably, the carbon atoms marked * is derived from the D-configuration and is conveniently referred to as the 'D-phenylglycine derivative'.

Since the compounds of the formula (I)) and their salts are intended for use in pharmaceutical compositions it will readily be understood that they are each provided in substantially pure form, for example at least 60% pure, more suitably at least 75% pure and preferably at least 85%, especially at least 95% pure. Impure preparations of the compounds of the formula (I) and their salts may be used for preparing the more pure forms used in the pharmaceutical compositions, these less pure preparations of the compounds of formula (I) and their salts should contain at least 1%, more suitably at least 5% and preferably from 10 to 49% of a compound of the formula (I) or their salts.

More particularly the present invention provides a class of bicyclic β-lactam of formula (II) or a pharmaceutically acceptable salt or in vivo hydrolysable ester thereof:

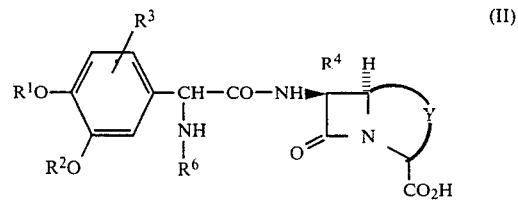
(II)

wherein $R^1$, $R^2$, $R^3$ and $R^4$ are as hereinbefore defined;
$R^6$ is hydrogen or a group $—COR^7$ or $—CO—NR^8—R^7$ wherein $R^7$ is an optionally substituted hydrocarbon or heterocyclic group and $R^8$ is hydrogen or $C_{1-6}$ alkyl;
and Y is

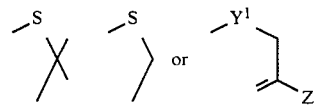

wherein $Y^1$ is oxygen, sulphur or $—CH_2—$ and Z represents hydrogen, halogen, or an organic group such as $C_{1-4}$ alkoxy, $—CH_2Q$ or $—CH=CH—Q$ wherein Q represents hydrogen, halogen, hydroxy, mercapto, cyano, carboxy, carbamoyloxy, carboxylic ester, $C_{1-4}$ alkyloxy, acyloxy, aryl, a heterocyclyl group bonded via carbon, a heterocyclylthio group or a nitrogen containing heterocyclic group bonded via nitrogen.

The term 'heterocyclic' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$) alkyl, aryl or oxo groups.

Suitable pharmaceutically acceptable salts of the compounds of formula (II) include metal salts, eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Examples of suitable pharmaceutically acceptable in vivo hydrolysable ester groups include those which break down readily in the human body to leave the parent acid or its salt. Suitable ester groups of this type include those of part formula (i), (ii) and (iii):

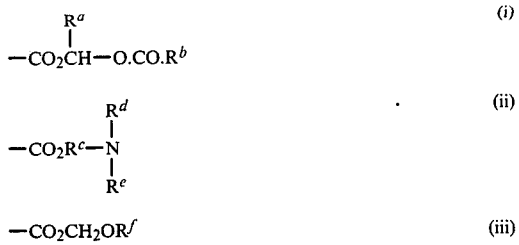

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups; $R^c$ represents ethylene optionally substituted with a methyl or ethyl group - $R^d$ and $R^e$ independently represent $C_{1-6}$ alkyl; $R^f$ represents $C_{1-6}$ alkyl. Examples of suitable in vivo hydrolysable ester group include for example acyloxyalkyl group such as acetoxymethyl, pivaloyloxy-methyl, α-acetoxyethyl and α-pivaloyoxyethyl groups; alkoxycarbonyloxyalkyl groups, such as ethoxycarbonyl-oxymethyl and α-ethoxycarbonyloxyethyl; dialkylamino-alkyl especially di-loweralkylamino alkyl groups such as dimethylaminoethyl, diethyl-aminomethyl or diethylaminoethyl; lactone group such as phthalidyl and dimethoxyphthalidyl; and esters linked to a second β-lactam antibiotic or to a β-lactamase inhibitor.

Suitably $R^6$ is a group —$COR^7$ wherein $R^7$ is as hereinbefore defined.

Suitably $R^6$ is a group —CO—$NR^8$—$R^7$ wherein $R^7$ and $R^8$ are as hereinbefore defined.

Suitable optional substituents for the hydrocarbon and heterocyclic groups for $R^7$ include $C_{1-6}$ alkyl, heterocyclic, amino, $C_{1-6}$ akkanoyl-amino, mono and di($C_{1-6}$) alkylamino, hydroxy, $C_{1-6}$ alkoxy, mercapto, $C_{1-6}$ alkylthio, heterocyclyl-thio, arylthio, sulphamoyl, carbamoyl, amidino, guanidino, nitro, chloro, bromo, fluoro, carboxy and salts and esters thereof, $C_{1-6}$ alkanoyloxy, aryl-carbonyl, alkylcarbonyl aralkyloxy and heterocyclylcarbonyl.

Suitably $R^8$ is methyl or hydrogen.

Preferably $R^8$ is hydrogen.

Preferred values for Y in the compounds of formula (I) are —S—$C(CH_3)_2$— and —S—$CH_2$—$C(CH_2Q)$=, ie when the compound of formula (I) is a derivative of a penicillin and cephalosporin.

A partiularly preferred value for Y is —S—$C(CH_3)_2$—.

A further preferred value for Y is —S—$CH_2$—CZ=. wherein Z is as hereinbefore defined.

Suitable values for Q in the compounds of the formula (I) include the acetoxy, heterocyclylthio group, and nitrogen containing heterocyclic group bonded via nitrogen.

More suitably Q and Q' represent acetoxy or a heterocyclylthio group.

The heterocyclylthio group may suitably be represented by the formula:

—S—Het wherein 'Het' is a five or six membered heterocyclic ring containing from 1 to 4 atoms selected from N, O, and S substituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylalkyl, trifluoromethyl, hydroxy, halogen, oxo, (subst)aminoalkyl, and alkylsulphonic acid, or two substituents may be linked to form the residue of a heterocyclic or carbocyclic ring.

Examples of the group 'Het' include unsubstituted and substituted imidazolyl, triazolyl, tetrazolyl, thiazolyl, thiadiazolyl, thiatriazolyl, oxazolyl, triazinyl and oxadiazolyl.

Suitable groups 'Het' include unsubstituted and substituted 1,2,3-triazolyl; 1,2,4-triazolyl; tetrazolyl; oxazolyl; thiazolyl; 1,3,4-oxadiazolyl; 1,3,4-thiadiazolyl, or 1,2,4-thiadiazolyl. Preferably the heterocyclylthio group is 1-methyl-1H-tetrazol-5-ylthio, 2-methyl-1,3,4-thiadiazol-5-ylthio, 1-carboxymethyl-1H-tetrazol-5-ylthio or 6-hydroxy-2-methyl-5-oxo-2H-1,2,4-triazin-3-ylthio.

The nitrogen containing heterocyclic group bonded via nitrogen is suitably a pyridinium group unsubstituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, $C_{1-6}$ alkylsulphonyl, sulphonylalkyl, carbamoylmethyl, carbamoyl, trifluoromethyl, hydroxy, halogen, oxo, dialkylamino alkyl and aminoalkyl.

Some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

One suitable sub-group within the present invention provides a compound of formula (III) or a pharmaceutically acceptable salt or in vivo hydrolysable ester thereof:

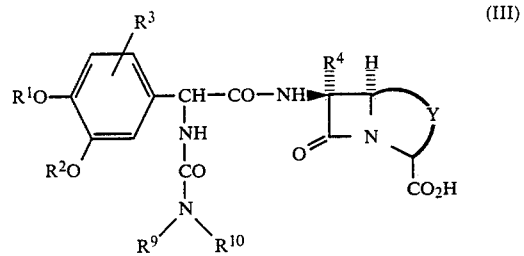

wherein $R^1$, $R^2$, $R^3$, $R^4$ and Y are as hereinbefore defined and $R^9$ is hydrogen or a $C_{1-6}$ alkyl group and $R^{10}$ is an optionally substituted 5- or 6-membered heterocyclic group containing one or two nitrogen heteroatoms; or $R^9$ and $R^{10}$ together with the nitrogen atom to which they are attached form an optionally substituted five- or six-membered heterocyclic group containing one or two nitrogen heteratoms.

Suitable substituents for the 5- or 6-membered heterocyclic group of $R^{10}$ or $R^9$ and $R^{10}$ together include the optionally substituted alkyl, alkenyl, alkynyl, cycloalkyl or cycloalkenyl group; optionally substituted phenyl, oxo; the hydroxy group optionally substituted by alkyl, alkenyl, cycloalkyl, phenyl, pyridyl, pyrimidyl or benzyl; the optionally substituted mercapto group, the alkylsulphonyl group; the substituted imino group; or the amino group optionally substituted by an alkyl, alkenyl, cycloalkyl, phenyl, substituted phenyl or benzyl group. Alternatively two substituents on the ring may form the residue of a further carbocyclic or heterocyclic ring.

One preferred sub-group within the present invention provides a compound of formula (IV) or a pharmaceutically acceptable salt or in vivo hydrolysable ester thereof.

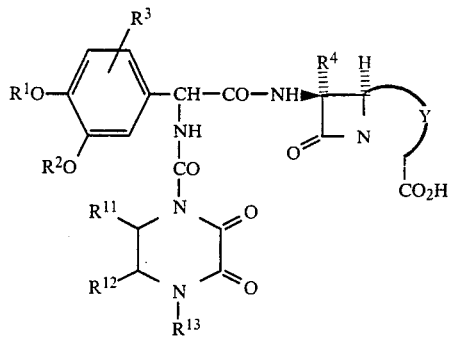

(IV)

wherein $R^1$, $R^2$, $R^3$, $R^4$ and Y are as hereinbefore defined and $R^{11}$ and $R^{12}$ are the same or different and each represents hydrogen, $C_{1-6}$ alkyl, substituted $C_{1-6}$ alkyl, halogen, carboxy, hydroxy, amino, or $C_{1-6}$ alkoxy or $R^{11}$ and $R^{12}$ together from the residue of a 5 or 6 membered carbocyclic or heterocyclic ring; and $R^{13}$ represents hydrogen, $C_{1-6}$ alkyl, substituted $C_{1-6}$ alkyl, aryl or aralkyl.

Suitably $R^{11}$ and $R^{12}$ are both $C_{1-6}$ alkyl or hydrogen.
Preferably $R^{11}$ and $R^{12}$ are both hydrogen.
Suitably $R^{13}$ is $C_{1-6}$ alkyl.
Preferably $R^{13}$ is ethyl.

Specific compounds within this invention include the following and pharmaceutically acceptable salts and in-vivo hydrolysable esters thereof:

Sodium 6,β-[D,L-2-(2-chloro-4,5-dihydroxyphenyl)-2-(2,3-dioxo-4-ethylpiperazin-1-ylcarbonylamino)acetamido]penicillanate;

Sodium 6,β[D,L-2-(2-chloro-4,5-diacetoxyphenyl)-2-(2,3-dioxo-4-ethylpiperazin-1-ylcarbonylamino)acetamido]bisnorpenicillanate;

6,β-[D,L-2-Amino-2-(2-chloro-4,5-diacetoxyphenyl-)acetamido]penicillanic acid;

Sodium 6,β-[D,L-2-(2-chloro-4,5-diacetoxyphenyl)-2-(2,3-dioxo-4-ethylpiperazin-1-ylcarbonylamino)acetamido]-6,α-methoxypenicillanate;

Sodium 6,β-[D,L-2-(2-chloro-4,5-diacetoxyphenyl)-2-2,3-dioxo-4-ethylpiperazin-1-ylcarbonylamino)acetamido]-6,α-formamidopenicillanate;

Sodium 6,β-[D-2-(2-chloro-4,5-diacetoxyphenyl)-2-(2,3-dioxo-4-ethylpiperazin-1-ylcarbonylaminoacetamido]-6,α-formamidopenicillanate;

Sodium 6,β-[D,L-2-(4,5-diacetoxy-2-fluorophenyl)-2-(2,3-dioxo-4-ethylpiperazin-1-ylcarbonylamino)acetamido]penicillanate;

Sodium 6,β-[D-2-(4,5-diacetoxy-2-fluorophenyl)-2-(2,3-dioxo-4-ethylpiperazin-1-ylcarbonylamino)acetamido]-6,α-formamidopenicillanate;

Sodium 6,β-[D-2-(2-chloro-4,5-diacetoxyphenyl)-2-(2,3-dioxo-4-ethyl-piperazin-1-ylcarbonylamino)acetamido]-penicillanate;

Sodium 6,β-[D,L-2-(2-bromo-4,5-diacetoxyphenyl)-2-(2,3-dioxo-4-ethylpiperazin-1-ylcarbonylamino)acetamido]-penicillanate;

Sodium 6,β-[D-2-(4,5-dihydroxy-2-fluorophenyl)-2-(2,3-dioxo-4-ethylpiperazin-1-ylcarbonylamino)acetamido]-penicillanate;

Sodium 6,β-[D-2-(2-chloro-4,5-dihydroxyphenyl)-2-(2,3-dioxo-4-ethyl-piperazin-1-ylcarbonylamino)acetamido]-6,α-formamidopenicillanate 7β[D-2-(2-Bromo-4,5-diacetoxyphenyl)-2-[(4-ethyl-2,3-dioxopiperazin-1-yl)carbonylamino]acetamido]-7α-formamidocephalosporanate, sodium salt;

7β[D-2-(2-chloro-4,5-diacetoxyphenyl)-2-[4-ethyl-2,3-dioxopiperazin-1-yl)carbonylamino]acetamido]-7α-formamidocephalosporanate, sodium salt;

7β-[D-2-(2-chloro-4,5-diacetoxyphenyl-2-[(4-ethyl-2,3-dioxopiperazin-1-yl)carbonylamino]acetamido]-7α-formamido-3[(1-methyl-1H-tetrazol-5-yl)thiomethyl]ceph-3-em-4-carboxylic acid, sodium salt;

Sodium 6,-β-[D-2-(2-fluoro-4,5-dihydroxyphenyl)-2-(2,3-dioxo-4-ethyl-piperazin-1-ylcarbonylamino)acetamido]-6,α-formamidopenicillanate;

or

7β-[D-2-(2-fluoro-4,5-diacetoxyphenyl)-2-[4-(ethyl-2,3-dioxoperazin-1-yl)carbonylamino]acetamido]-7α-formamidocephalosporonate, sodium salt.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a compound of formula (II) above together with a pharmaceutically acceptable carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, eg cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight active agent, preferably from 10-60% by weight, of the active material, depending on the method of administration. Where the compositions are in unit dosage form, each unit will preferably contain from 50-500 mg of the active ingredient. The dosage as employed for adult human treatment will preferably range from 100 to 10000 mg per day, for instance 1500 mg per day depending on the route and frequency of administration. Such a dosage corresponds to 1.5 to 50 mg/kg per day. Suitably the dosage for adult human treatment is from 5 to 20 mg/kg per day.

The antibiotic compound according to the present invention may be the sole therapeutic agent in the compositions of the invention or is present in combination with other antibiotics and/or β-lactamase inhibitory agents.

Advantageously the compositions also comprise a compound of formula (V) or a pharmaceutically acceptable salt or ester thereof:

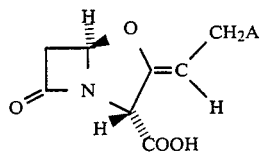

(V)

wherein A is hydroxyl, substituted hydroxyl, thiol, substituted thiol, amino, mono- or di-hydrocarbyl substituted amino, or mono- or di-acylamino.

A further advantageous composition comprises an antibacterially effective amount of an antibiotic compound according to the invention together with a β-lactamse inhibitory amount of a β-lactamase inhibitor of formula (VI) or a pharmaceutically acceptable salt or in vivo hydrolysable ester thereof:

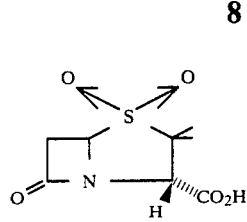

(VI)

and a pharmaceutically acceptable carrier or excipient.

Further suitable β-lactamase inhibitors include 6β-bromopenicillanic acid and salts and in vivo hydrolysable esters and 6β-iodopenicillanic acid and salts and in vivo hydrolysable esters thereof.

Such compositions of this invention which include a β-lactamase inhibitory amount of a β-lactamase inhibitor are formulated in a conventional manner using techniques and procedures per se known in the art.

The present invention also includes a method of treating bacterial infections in humans and animals which comprises the administration of a therapeutically effective amount of an antibiotic compound of this invention.

The antibiotic compounds of the present invention are active against a broad range of gram positive and gram negative bacteria, in particular they are useful for treatment of respiratory tract and urinary tract infections in humans and mastitis in cattle.

The present invention further provides a process for the preparation of a compound having partial structure (I) which process comprises reacting a compound having partial structure (VII):

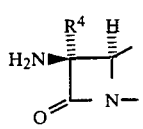

(VII)

wherein any reactive groups may be protected and wherein the amino group is optionally substituted with a group which permits acylation to take place and $R^4$ is as hereinbefore defined, with an N-acylating derivative of an acid of partial structure (VIII):

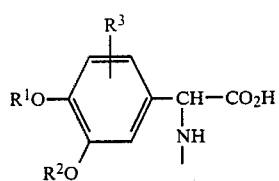

(VIII)

wherein $R^1$, $R^2$ and $R^3$ are as hereinbefore defined and thereafter where necessary removing any protecting groups.

Suitable groups which permit acylation to take place and which are optionally present on the amino group of the starting material of the formula (VII) include N-silyl, N-stannyl and N-phosphorus groups, for example trialkylsilyl groups such as trimethylsilyl, trialkyltin groups such as tri-n-butyltin, groups of formula —P.-$R^aR^b$ wherein $R^a$ is an alkyl, haloalkyl, aryl, aralkyl, alkoxy, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P(OC$_2$H$_5$)$_2$, —P(C$_2$H$_5$)$_2$,

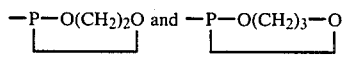

Suitable silylating agents include halosilanes or silazanes of the formulae:

$L_3-Si-U$; $L_2-Si-U_2$; $L_3-Si-NL_2$; $L_3-Si-N-H-Si-L_3$; $L_3-Si-NH-COL$; $L_3-Si-N-H-CO-NH-Si-L_3$; $L-NH-CO-NH-Si-L_3$;

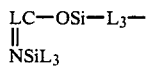

wherein U is a halogen and the various groups L which may be the same or different, each represents alkyl, alkoxy, aryl, or aralkyl. Preferred silylating agents are silyl chlorides, particularly trimethylchlorosilane, and dimethyldichlorosilane.

A reactive N-acylating derivative of the acid (VIII) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example, tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{1-6})$-1,2,alkylene oxide—such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, aqueous tetrahydrofuran, ethyl, acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (VIII) or a salt thereof with a halogenating (eg chlorinating or brominating) agent such as phosphorus pentachloride, thionyl chloride or oxalyl chloride.

Alternatively, the N-acylating derivative of the acid (VIII) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids), or aliphatic or aromatic sulphonic acids (such as p-toluenesulphonic acid). When a symmetrical anhydride is employed, the reaction may be carried out in the presence of 2,6-lutidine as catalyst.

Alternative N-acylating derivatives of acid (VIII) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, $N^1$-hydroxybenzotriazole or 8-hydroxyquinoline; or amides such as N-acylsaccharins, N-acylthiazolidin-2-thione or N-acylphthalimides; or an alkylidene iminoester prepared by reaction of the acid (VIII) with an oxime.

Other reactive N-acylating derivatives of the acid (VIII) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3-C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

Suitably the compound having partial structure (VII) is a compound of formula (IX):

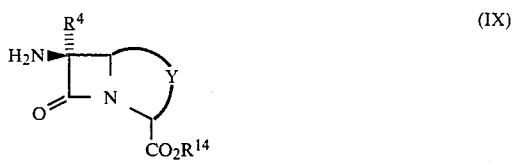

wherein $R^4$ and Y are as hereinbefore defined and $R^{14}$ is a carboxyl blocking group.

Suitable carboxyl-blocking derivatives for the group $-CO_2R^{14}$ in formula (IX) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-protecting groups are those which may be removed under conventional conditions. Such groups for $R^x$ include benzyl, p-methoxybenzyl, 2,4,6-trimethylbenzyl, 3,5-di-t-butyl-4-hydroxy-benzyl, benzoylmethyl, p-nitrobenzyl, 4-pyridylmethyl, 2,2,2-trichloroethyl, 2,2,2-tribromoethyl, allyl, acetonyl, t-butyl, t-amyl, diphenylmethyl, triphenylmethyl, adamantyl, 2-benzyl-oxyphenyl, 4-methylthiophenyl, tetrahydrofur-2-yl, tetrahydropyran-2-yl, pentachlorophenyl, p-toluene-sulphonylethyl, methoxymethyl, a silyl, stannyl or phosphorus-containing group, an oxime radical of formula $-N=CHR^o$ where $R^o$ is aryl or heterocyclic, or an in vivo hydrolysable ester radical.

The carboxyl group may be regenerated from any of the above esters by usual methods appropriate to the particular $R^{14}$ group, for example, acid-and base-catalysed hydrolysis, or by enzymically-catalysed hydrolysis, or by hydrogenation.

Suitably the compound having partial structure (VIII) is a compound of formula (X):

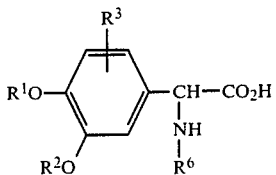

wherein $R^1$, $R^2$, $R^3$ and $R^6$ are as hereinbefore defined.

Compounds of formula (II) wherein $R^6$ is a group —$COR^7$ or —$CO$—$NR^8$—$R^7$ may also suitably be prepared by reacting a compound of formula (XI):

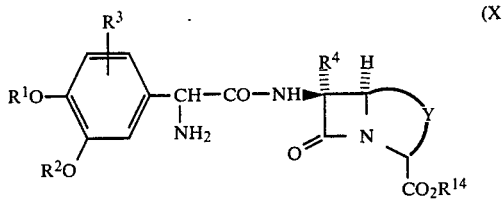

wherein $R^1$, $R^2$, $R^3$, $R^4$, Y and $R^{14}$ are as hereinbefore defined and wherein any reactive groups may be protected; and wherein the amino group is optionally substituted with a group which permits acylation to take place, with an N-acylating derivative of an acid of formula (XII) or (XIII):

wherein $R^7$ and $R^8$ are as hereinbefore defined and wherein any reactive groups may be protected,
and
thereafter, if necessary, carrying out one or more of the following steps:
  (i) removing any carboxyl-blocking groups $R^{14}$;
  (ii) removing any protecting groups on the side chain group;
  (iii) converting the product into a salt or in vivo hydrolysable ester thereof.

Suitable groups $R^{14}$ and N-acylating derivatives are as hereinbefore defined.

Compounds having partial structure (I) wherein $R^4$ is:
  (i) methoxy or
  (ii) formamido may suitably be prepared by reacting a compound having partial structure (XIV):

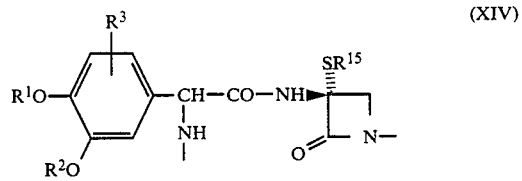

wherein any reactive groups may be protected, $R^1$, $R^2$ and $R^3$ are as hereinbefore defined and $R^{15}$ is $C_{1-6}$ alkyl, aryl or benzyl; in the presence of a metal ion such as mercury, silver, thallium, lead or copper with
  (a) methanol; or
  (b) ammonia or an ammonium salt and thereafter with a formylating agent.

Suitable examples of the alkyl group for $R^{15}$ include $C_{1-6}$ alkyl groups such as methyl, ethyl, n-, or iso-propyl, and n-, sec-; iso-, or tert-butyl groups.

A preferred alkyl group for $R^{15}$ is methyl.

Suitable examples of the aryl group $R^{15}$ include phenyl, optionally substituted with $C_{1-6}$ alkyl, $C_{1-6}$ alkoxy, halogen, or nitro. Preferred aryl groups for $R^{19}$ include phenyl, o-, m- or p-methylphenyl, o-, m- or p-nitrophenyl, in particular p-methylphenyl.

Suitable solvents in which the reaction may be performed include for example, diethylether, tetrahydrofuran, dimethylformamide, methanol and hexamethylphosphoramide. The reactions are generally carried out under an inert atmosphere and at moderate to low temperatures ie in the range $-100°$ C. to 30° C. The course of the reaction may be followed by conventional methods such as thin layer chromatography and terminated when an optimum quantity of product is present in the reaction mixture.

The preferred metal ion for use in the above process is the mercuric ion, aptly in the form of mercuric acetate.

Suitable formulating agents include mixed anhydrides such as formic acetic anhydride. The reaction may suitably be carried out in a temperature in the range $-50<C.$ to $30<C.$ in aprotic solvent such as, for example, dichloromethane, chloroform, dimethylformamide, tetrahydrofuran, hexamethylphosphoramide or dimethylsulphoxide, in the presence of a tertiary base. A preferred tertiary base employed in the reaction is a base of the pyridine type, such as pyridine, lutidine or picoline.

It will be appreciated that the process described above employing the compound having partial structure (XIV) proceeds via an acylimine intermediate; other processes proceeding via such an intermediate are also included herein. Examples of such processes are described for example in our copending European Pat. No. 84300338.5.

A suitable compound of partial structure XIV is a compound of formula XIVA:

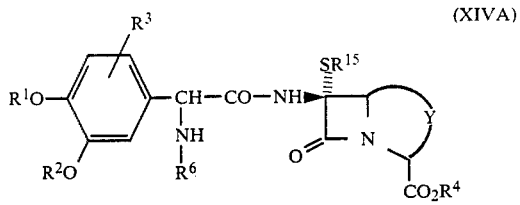

wherein $R^1$, $R^2$, $R^3$, $R^6$, $R^{14}$, $R^{15}$ and Y are as hereinbefore defined.

The acid having partial structure (VIII) and N-acylating derivatives thereof are novel compounds and form a further aspect of the present invention.

A particularly useful acid having partial structure (VIII) is the phenyl glycine derivative (XV):

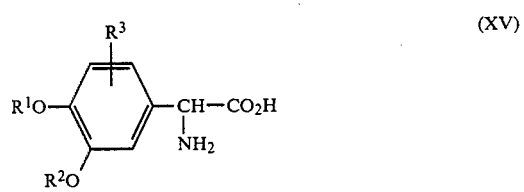

wherein $R^1$, $R^2$ and $R^3$ are hereinbefore defined.

The phenylglycine derivative (XV) may suitably be prepared by treating a compound of formula (XVI):

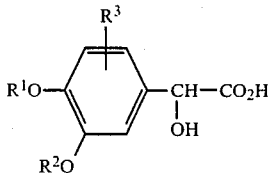

with ammonia.

The compound of formula (XVI) may suitably be prepared by reacting by known means glyoxylic acid in the presence of hydroxide ion with a compound of formula (XVII):

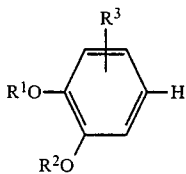

The preparation of a compound of formula (XVI) and subsequent conversion to a compound of formula (XV) is suitably carried out in a single reaction mixture.

The antibiotic compounds of the present invention are active against a wide range of gram negative and gram positive organisms including *E. coli* such as, for example ESS, JT4, JT425 and NCTC 10418; Pseudomonas Spp. such as *Ps.aeruginosa* for example 10622 and Dalgleish; *Serratia marcescens* US32; *Klebsiella aerogenes* A; *Enterobacter cloacae* N1; *P.mirabilis* such as, for example C977 and 889; *P.morganii, P.rettgeri; B.subtilis; Staph. aureus* such as, for example Oxford and Russell; *N.catarrhalis* 1502; *Strep faecalis* I; *β-Haemolytic Strep* CN10. The MIC data included in the following examples is representative of the activity of the compounds of the present invention.

The following Examples illustrate the preparation and use of the compounds of the present invention.

PREPARATION 1

2-Chloro-4,5-dihydroxymandelic acid

Sulphuryl chloride (0.8 ml) was added to a solution of 3,4-dihydroxymandelic acid (1.84 g, 10 mmol) in warm acetic acid (20 ml). The mixture was stirred for two hours then poured into water and extracted with ethyl acetate (6×40 ml). The extracts were washed with saturated brine (50 ml), dried and evaporated to a crystalline mass (2.36 g) which was recrystallised from ethyl acetate-cyclohexane, 0.97 g, 44%, mp 177°, δ[(CD$_3$)$_2$SO] 5.15(1H, s, CH), 6.71 and 6.85(2H, 2×s, Ar), 8.4–9.8(3H, m, 2×OH, CO$_2$H).

EXAMPLE 1

(a) 2-Chloro-4,5-dihydroxyphenylglycine

Aqueous ammonia (Sp.Gr 0.88, 37.5 ml) was added dropwise to an ice bath cooled 50% w/v aqueous glyoxylic acid solution (11.25 ml) at <10°. When the addition was complete the solution was heated at 50° for 15 minutes, 4-chlorocatechol (21.7 g) and more aqueous ammonia (12.5 ml) added, then heated at 60° for 4 hours. The solution was allowed to cool, reduced to ca. half volume in vacuo, washed with ethyl acetate (3×40 ml), adjusted to pH 5.5(conc, HCl) and set aside at 0° overnight. The solid was collected, washed with water and methanol, then dried, 2.76 g. The crude product was suspended in water (30 ml), conc. hydrochloric acid added to give a clear solution, treated with decolourising charcoal, filtered, adjusted to pH 5.5(40% sodium hydroxide solution) and left to crystallise at 0°. The product was collected, washed with water and acetone then dried, 2.53 g, 16% δ(CF$_3$CO$_2$H), 5.5–5.8(1H, m, CH), 7.10(2H, s, Ar), 7.70 (3H, broad, NH$_3$) Found: C, 40.48; H, 4.27 Cl, 15.03; N, 5.91%. C$_8$H$_8$ClNO$_4$. H$_2$O requires: C, 40.78; H, 4.28; Cl, 15.05; N, 5.95%.

(b) D,L-2-(2-Chloro-4,5-dihydroxyphenyl)-2-(2,3-dioxo-4-ethylpiperazin-1-ylcarbonyl amino)acetic acid D,L-2-Chloro-4,5-dihydroxyphenylglycine (217 mg, 1 mmole) was suspended in trimethylsilyl diethylamine (2 ml), stirred at 80° for 40 minutes then evaporated to dryness in vacuo. The residue in dichloromethane (8 ml) was cooled to −10° then treated dropwise with 2,3-dioxo-4-ethylpiperazin-1-ylcarbonyl chloride (205 mg, 1 mmole) in dichloromehane (1 ml). The reation was stirred for 90 minutes while warming to room temperature then water (5 ml) and acetone were added and the mixture stirred at pH 1.5 for 20 minutes. The mixture was concentrated in vacuo and the aqueous residue adjusted to pH 7.5, washed with ethyl acetate, acidified to pH 1 and extracted with ethyl acetate to give the title compound, 330 mg 85%, mp 208°–211° (dec), δ(CD$_3$OD) 1.16(3H, t, J 7.5 Hz, NCH$_2$CH$_3$), 3.50 (2H, q, J 7.5 Hz, NCH$_2$CH$_3$), 3.65 and 3.95 (4H, 2 m, 2×NCH$_2$), 5.63 (1H, d, J 6.5 Hz, CHNH), 6.77(2H, s, Ar), 9.73(1H, d, J6.5 Hz, CHNH).

(c) D,L-2-(2-Chloro-4,5-diacetoxyphenyl)-2-(2,3-dioxo-4-ethylpiperazin-1-ylcarbonylamino)acetic acid D,L-2-(2-Chloro-4,5-dihydroxyphenyl)-2-(2,3-dioxo-4-ethylpiperazin-1-ylcarbonylamino)acetic acid (530 mg 1.3 mmole) in water (10 ml) and THF (4 ml) was adjusted to pH 7.5 with 5% sodium carbonate then acetic anhydride (330 μl, 2.5 equivalents) added dropwise. The mixture was maintained at pH 6.5 with 5% sodium carbonate for 25 minutes then acidified to pH 1.5 and extracted with ethyl acetate. The extracts were combined, dried and evaporated to give the title compound, 640 mg, 98%, mp 181°–184° (dec) ν$_{max}$ (Nujol) 1785, 1775, 1745, 1720, 1715 and 1655 cm$^{-1}$, δ(CD$_3$OD) 1.16 (3H, t, J7 Hz, NCH$_2$CH$_3$), 2.20 (6H, s, 2×OCOCH$_3$), 3.3–4.1 (6H, m, 3×NCH$_2$), 5.78 (1H, d, J 6.5 Hz, CHNH), 7.29(2H, s, Ar), 9.93(1H, d, J6.5 Hz, CHNH).

(d) Benzyl 6,β-[D,L-2-(2-chloro-4,5-diacetoxyphenyl)-2-(2,3-dioxo-4-ethylpiperazin-1-ylcarbonylamino)acetamido]-penicillanate Dicyclohexylcarbodiimide (106 mg 0.5 mmole) in dichloromethane (1 ml) then a suspension of DL-2-(2-chloro-4,5-diacetoxyphenyl)-2-(2,3-dioxo-4-ethylpiper--azin-1-ylcarbonylamino)acetic acid (235 mg. 0.5 mmole) in THF (15 ml) were added to benzyl 6β-aminopenicillanate (153 mg, 0.5 mmole) in dichloromethane (15 ml) cooled to −10°. The reaction was stirred for 2.5 hours while warming to room temperature then evaporated to dryness in vacuo. Dichloromethane was added to the residue, which was filtered and the filtrate washed with dilute sodium bicarbonate, dilute hydrochloric acid, and brine then evaporated to a foam, 431 mg. This was chromatographed on silica gel eluting with 25% hexane in ethyl acetate, 257 mg 68%, $\delta_{max}$ (CH$_2$Cl$_2$) 1780, 1745, 1715, 1695 cm$^{-1}$, $\delta$[(CD$_3$)$_2$CO] 1.13 (3H, t, J7 Hz, NCH$_2$C$\underline{H}_3$), 1.37 and 1.47 (6H, 2×s, 2×2CH$_3$), 2.21(6H, s, 2×OCOCH$_3$), 3.41(2H, q, J7 Hz, NC$\underline{H}_2$CH$_3$), 3.5–4.2(4H, 2×m, 2×NCH$_2$), 4.35(1H, s, 3H), 5.12(2H, s, OCH$_2$), 5.4–5.6(2H, m, 5 and 6H), 5.88 (1H, 2×d, J7 Hz, C$\underline{H}$NH), 7.2–7.4(7H, m, Ph, Ar)9.80(1H, 2×d, J7 Hz, CH$\underline{N}$H).

(e) Sodium 6,β-[D,L-2-(2-chloro-4,5-dihydroxyphenyl)-2-(2,3-dioxo-4-ethylpiperazin-1-ylcarbonylamino)acetamido penicillanate Benzyl 6,β-[D,L-2-(2-chloro-4,5-diacetoxyphenyl)-2-(2,3-dioxo-4-ethylpiperazin-1-ylcarbonylamino)acetamido]penicillanate (200 mg) in THF (10 ml) was hydrogenated in the presence of 10% palladium on carbon (210 mg). The mixture was filtered, the filtrate evaporated to dryness and the residue dissolved in aqueous sodium bicarbonate to pH7. The aqueous solution was freeze dried to give a mixture of the title compound and its diacetate, 130 mg. The mixture (100 mg) was stirred in aqueous sodium bicarbonate solution until hplc (u-BONDAPAK C$_{18}$ reverse phase column eluted with 40% methanol in pH 4.5 0.05N ammonium acetate buffer at 2 ml/min) showed hydrolysis of the acetate was complete. The solution was washed with ethyl acetate, acidified to pH 1.5, brine added and extracted with ethyl acetate. The extracts were dried over anhydrous magnesium sulphate then back extracted into water at pH 6.6 and freeze dried, 38 mg, $\nu_{max}$ (KBr) 1770, 1715 and 1680 cm$^{-1}$, $\delta$(D$_2$O) 1.15(3H, t, J7.5 Hz, NCH$_2$C$\underline{H}_3$), 1.32, 1.43 and 1.45(6H, 3×s, 2×2CH$_3$), 3.48(2H, q, J7.5 Hz, NC$\underline{H}_2$CH$_3$), 3.7and 4.0(4H, 2×m, 2×NCH$_2$), 4.17 and 4.19(1H, 2×s, 3H), 5.47 and 5.49(2H, 2×q, J4.5 Hz, 5H and 6H), 5.73(1H, 2×s, C$\underline{H}$NH), 6.9–7.0(2H, m, Ar). MIC against *Klebsiella aerogenes* A <0.06 μg/ml.

EXAMPLE 2

(a) Benzyl 6,β-[D,L-2-(2-chloro-4,5-diacetoxyphenyl)-2-(2,3-dioxo-4-ethyl piperazin-1-ylcarbonylamino)acetamido]bisnorpenicllanate Dicyclohexylcarbodiimide (106 mg, 0.5 mmole) in dichloromethane (1 ml) then a suspension of D,L-2-(2-chloro-4,5-diacetoxyphenyl)-2-(2,3-dioxo-4-ethylpiperazin-1-ylcarbonylamino)acetic acid (235 mg, 0.5 mmole) in THF (20 ml) were added to benzyl 6-aminobisnorpenicillanate (139 mg, 0.5 mmole) in dichloromethane (15 ml) cooled to −10°. The mixture was stirred for 2.5 hours allowing to warm to room temperature and then evaporated to dryness in vacuo. Ethyl acetate (40 ml) was added to the residue, the mixture filtered and the filtrate washed with dilute sodium bicarbonate solution, dilute hydrochloric acid and brine then dried and evaporated to a foam, 420 mg, which was chromatographed on silica gel eluting with 10% hexane in ethyl acetate, then crystallised from ethyl acetate-ether, 115 mg, $\nu$max(CH$_2$Cl$_2$) 1785, 1745, 1720 and 1695 cm$^{-1}$, $\delta$(CDCl$_3$) 1.22(3H, t, J7.3 Hz, NCH$_2$C$\underline{H}_3$), 2.27 (6H, s, 2×OCOCH$_3$), 3.4(2H, m, 2×2H), 3.55(4H, m, 2×NCH$_2$), 4.1(2H, m, NCH$_2$), 4.95(1H, m, 3H), 5.18(2H, s, OCH$_2$) 5.32 and 5.33(1H, 2×d, J 15 Hz, 5H), 5.55 and 5.63 (1H, 2×d of d, J15 Hz and 8.5 Hz, 6H), 5.89 and 5.90(1H, 2×d, J9 Hz, C$\underline{H}$NH), 6.76(1H, d, J8.5 Hz, 6NH), 7.2–7.5(7H, m, Ph and Ar), 10.04 and 10.10 (1H, 2×d, J9 Hz, CH$\underline{N}$H).

(b) Sodium 6,β[D,L-2-(2-chloro-4,5-diacetoxy phenyl)-2-(2,3-dioxo-4-ethylpiperazin-1-ylcarbonylamino)acetamido]bisnorpenicllIanate Benzyl 6,β-[D,L-2-(2-chloro-4,5-diacetoxyphenyl)-2-(2,3-dioxo-4-ethylpiperazin-1-ylcarbonylamino)acetamido]bisnorpenicllanate (105 mg) in THF (10 ml) was hydrogenated in the presence of 10% palladium on carbon (0.1 g). The catalyst was filtered off and washed with THF and the filtrate evaporated to dryness in vacuo. The residue was dissolved in ethyl acetate, extracted with dilute sodium bicarbonate to pH 6.8 and freeze dried, 30 mg, $\nu_{max}$ (KBr) 1770, 1715 and 1680 cm$^{-1}$, $\delta$(D$_2$O) 1.18 (3H, t, J7.5 Hz, NCH$_2$C$\underline{H}_3$), 2.34(6H, s, 2×OCOCH$_3$), 3.30–3.43(2H, m, 2×2H), 3.50 (2H, q, J7.5 Hz, NC$\underline{H}_2$CH$_3$), 3.7 and 4.0 (4H, 2×m, 2×NCH$_2$), 4.85 (1H, m, 3H), 5.3–5.5(2H, m, 5 and 6H), 5.90(1H, m, C$\underline{H}$NH), 7.4–7.5(2H, m, Ar). MIC against *Klebsiella aerogenos* A <0.06 μg/ml.

EXAMPLE 3

(a) N-Benzyloxycarbonyl 2-chloro-4,5-dihydroxyphenylglycine

Acetic acid (27 ml), concentrated sulphuric acid (3 ml) then 4-chlorocatechol (5.06 g. 35 mmole) were added to N-benzyloxycarbonyl 2-hydroxyglycine (6.75 g, 30 mmole) cooled in an ice bath. The mixture was stirred for one hour then poured onto ice and ethyl acetate and adjusted to pH7 with saturated sodium carbonate solution. The aqueous layer was collected, washed with ethyl acetate (100 ml), acidified to pH2 and extracted with ethyl acetate (3×75 ml). The extracts were washed with water (2×75 ml) and brine (50 ml) dried and evaporated to a gum which was crystallised from chloroform-cyclohexane, 5.90 g, 56%, mp 144°–145°, $\delta$[(CD$_3$)$_2$CO] 5.06 (2H, s, OCH$_2$), 5.64(1H, d, J8 Hz, C$\underline{H}$NH), 6.6–7.0(1H, m, NH), 6.87 and 6.93(2H, 2×s, Ar), 7.30(5H, s, Ph) 8.0–9.4(3H, broad, 2×OH, CO$_2$H). Found: C. 54.29; H, 4.04; Cl, 9.71; N, 4.07%. C$_{16}$H$_{14}$ClNO$_6$ requires C, 54.63; H, 4.01; Cl, 10.08; N, 3.98%.

(b) N-Benzyloxycarbonyl 2-chloro-4,5-dihydroxyphenylglycine

N-Benzyloxycarbonyl 3,4-dihydroxyphenylglycine (0.79 g, 2.5 mmole) in acetic acid (10 ml) was treated with sulphuryl chloride (0.2 ml), stirred at room temperature for two hours then diluted with ethyl acetate (50 ml), washed with water (2×3 ml) and brine (20 ml), dried and evaporated to a gum which was crystallized from chloroform, 0.36 g, 41%, mp 141°–143°.

(c) N-Benzyloxycarbonyl 2-chloro-4,5-diacetoxyphenylglycine

N-Benzyloxycarbonyl 2-chloro-4,5-dihydroxyphenylglycine (1.76 g, 5 mmole) in water (30 ml) and THF (20 ml) was adjusted to pH 7.5 with saturated sodium carbonate solution. Acetic anhydride (1.2 ml) was added and pH 6.5 maintained with saturated sodium carbonate solution, after 15 minutes and again after a further 15 minutes more acetic anhydride (0.6 ml) was added. After another 15 minutes the solution was washed with ether (2×25 ml), acidified to pH 2.5 and extracted with ethyl acetate (3×30 ml). The extracts were washed with water (2×25 ml) and brine (20 ml) dried and evaporated to a foam, 1.87 g 86%, $\delta[(CD_3)_2CO]$ 2.20(6H, s, 2×OCOCH$_3$), 5.03(2H, s, OCH$_2$), 5.80(1H, d, J8 Hz, CHNH), 7.12(1H, d, J8 Hz, CHNH), 7.23(5H, s, Ph), 7.33 and 7.35(2H, 2×s, Ar), 9.57(1H, s, CO$_2$H).

(d) Benzyl 6,β[D,L-2-benzyloxycarbonylamino-2-(2-chloro-4,5-diacetoxyphenyl)-acetamido]penicllanate N-Benzyloxycarbonyl 2-chloro-4,5-diacetoxyphenylglycine (1.48 g, 3.4 mmole) in dichloromethane (20 ml) was added dropwise over 30 minutes to benzyl 6,β-aminopenicillanate (1.22 g, 4 mmole) and dicyclohexylcarbodiimide (0.91 g, 4.4 mmole) in dichloromethane (20 ml). The mixture was stirred for 2 hours, filtered and the filtrate washed with dilute hydrochloric acid (20 ml) and water (20 ml), dried and evaporated to a foam which was chromatographed on silica gel eluting with 25% ethyl acetate in cyclohexane, 1.45 g, 59%, $\nu_{max}$ (film) 1785, 1745, 1720, 1690, 1495, 1370, 1205 and 1140 cm$^{-1}$, $\delta[(CD_3)CO]$ 1.40 and 1.50 (6H, 2×s, 2×2CH$_3$), 2.23(6H, s, 2×OCOCH$_3$), 4.37(1H, s, 3H), 5.03(2H, s, OCH$_2$), 5.15(2H, s, OCH$_2$), 5.3–5.6(2H, m, 5 and 6H), 5.73(1H, d, J8 Hz, CHNH), 6.9–8.1(14H, m, 2×Ph, Ar, 2×NH).

(e) 6,β-[D,L-2-Amino-2-(2-chloro-4,5-diacetoxyphenyl)acetamido]penicillanic acid Benzyl 6,β-[D,L-2-benzyloxycarbonylamino-2-(2-chloro-4,5-diacetoxyphenyl)acetamido]penicllanate (1.45 g) and p-toluidine (0.21 g) in THF (20 ml) were diluted with water until just not cloudy, then hydrogenated in the presence of 10% palladium on carbon (1.5 g) for 75 minutes. The catalyst was replaced and hydrogenation continued for a further 45 minutes and the mixture filtered. The filtrate was concentrated in vacuo and the aqueous residue washed with ethyl acetate (2×25 ml) and ether (50 ml) then freeze dried, 0.49 g, 49%, $\nu_{max}$ (KBr) 1770, 1680, 1600, 1440, 1370, 1200, 1140, 1010 and 910 cm$^{-1}$, $\delta(D_2O)$ 1.36 and 1.41 (6H, 2×s, 2×2CH$_3$), 2.31(6H, s, 2×OCOCH$_3$), 4.13 and 4.17 (1H, 2×s, 3H), 5.3–5.55(2H, m, 5 and 6H), 5.59(1H, s, CHNH$_3^+$), 7.43 and 7.57 (2H, 2×s, Ar).

EXAMPLE 4

(a) Benzyl 6,β-[D,L-2-(benzyloxycarbonylamino)-2-(2-chloro-4,5-diacetoxyphenyl)acetamido]-6,α-methylthiopenicillanate N-Benzyloxycarbonyl, 2-LD-chloro-4,5-diacetoxyphenylglycine (1.87 g 4.3 mmole) in dichloromethane (15 ml) was added dropwise over one hour to an ice bath cooled solution of benzyl 6,β-amino-6,α-methylthiopenicillanate (1.94 g, 5.5 mmole) and dicyclohexylcarbodiimide (1.13 g) in dichloromethane (20 ml). The mixture was stirred overnight, filtered and the filtrate washed with dilute hydrochloric acid (10 ml), water (10 ml), sodium bicarbonate solution (10 ml) and water (10 ml), dried and evaporated to a foam which was chromatographed on silica gel eluting with 30% ethyl acetate in cyclohexane, to give the title compound, 1.01 g, 31%, $\delta[(CD_3)_2CO]$ 0.95, 1.02 and 1.18 (6H, 3×s, 2×2CH$_3$), 2.23(6H, s, 2×OCOCH$_3$), 2.28(3H, s, SCH$_3$), 4.38 and 4.43 (1H, 2×s, 3H), 5.02(2H, s, OCH$_2$), 5.15(2H, s, OCH$_2$), 5.42(2H, s, 5H), 5.78 and 5.82 (1H, 2×d, J8 Hz, CHNH), 7.05(1H, d, J8 Hz, CHNH), 7.24 and 7.30 (10H, 2×s, 2×Ph), 7.33 and 7.50(2H, 2×s, Ar), 8.55 and 8.80(1H, 2×s, CONH).

(b) Benzyl 6,β-[D,L-2-benzyloxycarbonylamino-2-(2-chloro-4,5-diacetoxyphenyl)-acetamido]-6,α-methoxypenicillanate Mercuric acetate (0.42 g) was added to a solution of benzyl 6β-[D,L-2-benzyloxycarbonylamino-2-(2-chloro-4,5-diacetoxyphenyl)acetamido]-6,α-methylthiopenicillanate (1.00 g) in methanol (10 ml). The mixture was stirred for 15 minutes, diluted with ethyl acetate (40 ml), filtered and the filtrate washed with water (2×20 ml) and brine (20 ml), dried and evaporated to a foam which was chromatographed on silica gel eluting with 50% ethyl acetate in cyclohexane, 0.85 g, 87%, $\delta[(CD_3)_2CO]$ 1.17, 1.27, 1.30 and 1.43(6H, 4×s, 2×2CH$_3$), 2.18(6H, s, 2×OCOCH$_3$), 3.30 and 3.42 (6H, 2×s, OCH$_3$), 4.38 and 4.43(1H, 2×s, 3H), 5.02(2H, s, OCH$_2$), 5.12 (2H, s, OCH$_2$), 5.47(1H, s, 5H), 5.82(1H, d, J8 Hz, CHNH), 6.7–7.2(1H, m, CHNH), 7.20(5H, s, Ph), 7.27 (5H, s, Ph), 7.40 and 7.52(2H, 2×s, Ar), 8.55 and 8.73(1H, 2×s, CONH).

(c) 6,β-[D,L-2-Amino-2-(2-chloro-4,5-diacetoxyphenylacetamido]-6,α-methoxypenicillanic acid Benzyl 6,β-[D,L-2-benxyloxycarbonylamino-2-(2-chloro-4,5-diacetoxy phenyl)acetamido]-6,α-methoxypenicillanate (0.84 g) in ethanol (20 ml) was diluted with water until just not cloudy then hydrogenated in the presence of 10% palladium on carbon (0.85 g) for one hour. The mixture was filtered, concentrated in vacuo and freeze dried, 0.44 g, 74%, $\nu_{max}$ (KBr) 1772, 1705, 1610, 1495, 1372 and 1210 cm$^{-1}$, $\delta(D_2O)$ 1.05, 1.25, 136 and 1.42(6H, 4×s, 2×2CH$_3$), 2.34 and 2.35(6H, 2×s, 2×OCOCH$_3$), 3.38 and 3.50(3H, 2×s, OCH$_3$), 4.20 and 4.24(1H, 2×s, 3H), 5.49 and 5.54(1H, 2×s, 5H), 5.61 and 5.65(1H, 2×s CH NH$^+_3$), 7.42, 7.57, 7.60 and 7.69 (2H, 4×s, Ar). H.p.l.c. analysis (μ-BONDAPAK C$_{18}$ reverse phase column, eluted with 24% methanol in pH 4.5 0.05M ammonium acetate buffer at 2 ml/min) showed a 2:1 mixture of D:L stereoisomers.

(d) Sodium 6,β-[D,L-2-(2-chloro-4,5-diacetoxyphenyl)-2-(2,3-dioxo-4-ethyl piperazin-1-ylcarbonylamino)acetamido]-6,α-methoxypenicillanate 2,3-Dioxo-4-ethylpiperazin-1-ylcarbonyl chloride (0.12 g 0.6 mmole) in acetone (5 ml) was added dropwise to 6,β-[D,L-2-amino-2-(2-chloro-4,5-diacetoxyphenyl)acetamido]-6,α-methoxypenicillanic acid (0.27 g, 0.5 mmole) in water (5 ml) maintained at pH 7.5±0.5 with saturated sodium carbonate solution. The solution was stirred for 10 minutes after the addition was complete then washed with ether (20 ml), acidified to pH 2.5 and extracted with ethyl acetate (3×15 ml). The extracts were washed with water (2×70 ml) and brine (15 ml), dried and evaporated to a foam (0.30 g). This in acetone (10 ml) was treated with 1.85N sodium 2-ethylhexanoate in 4-methylpentan-2-one (0.23 ml), diluted with ether (20 ml) and the precipitated sodium salt collected, washed with ether and dried in vacuo, 0.27 g, 75%, $\nu_{max}$ (KBr) 1770, 1712, 1680, 1610, 1490, 1395, 1370, 1265, 1200, 1140 and 1098 cm$^{-1}$, $\delta(D_2O)$ 1.0–1.5

(9H, m, 2×2CH₃, CH₂CH₃), 2.31 (6H, s, 2×OCOCH₃), 3.40 and 3.50 (3H, 2×s, OCH₃), 3.2–4.1(6H, m, 3×NCH₂) 4.16 and 4.21(1H, 2×s, 3H), 5.48 (1H, s, 5H), 5.89(1H, s, CHNH), 7.43 and 7.47 (2H, 2×s, Ar). H.p.l.c. analysis (μ-BONDAPAK C₁₈ reverse phase column eluted with 40% methanol in pH 4.5 0.05M ammonium acetate buffer at 2 ml/min) showed a 2:1 mixture of D:L steriosomers. MIC against *Proteus mirabilis* 889 4.0 μg/ml.

EXAMPLE 5

(a) Benzyl 6,β-[D,L-2-benzyloxycarbonylamino-2-(2-chloro-4,5-diacetoxyphenyl)acetamido]-6,α-formamido-penicillanate N-Benzyloxycarbonyl 2-chloro-4,5-diacetoxyphenylglycine (2.17 g, 5 mmole) in dichloromethane (5 ml) was added dropwise to benzyl 6,β-amino-6,α-formamidopenicillanate (1.75 g, 5 mmole) and dicyclohexylcarbodiimide (1.13 g 5.5 mmole) in dichloromethane (10 ml). The mixture was stirred overnight, filtered and the filtrate evaporated to a foam which was chromatographed on silica gel eluting with ethyl acetate in cyclohexane, 30% grading to 50%, 1.72 g, 45%, $\nu_{max}$ (film), 1775, 1735, 1690, 1485, 1365, 1260, 1200, 1135 and 905 cm⁻¹, δ[(CD₃)CO] 1.18, 1.25, 1.31 and 1.39 (6H, 4×s, 2×2CH₃), 2.25(6H, s, 2×OCOCH₃), 4.41 and 4.48(1H, 2×s, 3H), 5.04 and 5.07 (2H, 2×s, OCH₂), 5.18 and 5.19(2H, 2×s, OCH₂), 5.57 and 5.59(1H, 2×s, 5H), 5.80 and 5.85(1H, 2×d, J9 Hz, CHNH), 6.85–7.2(1H, m, CHNH), 7.25–7.45 (10H, m, 2×Ph), 7.45 and 7.51(2H, 2×s, Ar), 8.12(1H, s, NHCHO), 8.1–8.6(2H, m, NHCHO, CONH).

(b) 6,β-[D,L-2-Amino-2-(2-chloro-4,5-diacetoxyphenyl)acetamido]-6,α-formamidopenicillanic acid Benzyl 6,β-[D,L-2-benzyloxycarbonylamino-2-(2-chloro-4,5-diacetoxyphenyl)acetamido]-6,α-formamidopenicllanate (1.70 g) in THF (20 ml) was diluted with water until just not cloudy then hydrogenated in the presence of 10% palladium on carbon (1.5 g) for one hour, the catalyst was replaced and hydrogenated for a further hour. The mixture was filtered, THF removed from the filtrate in vacuo and the aqueous residue washed with ethyl acetate (2×50 ml) and ether (50 ml) then freeze dried to give the crude product, 0.63 g. This was chromatographed on HP20SS resin eluting with acetone in water, 0% grading to 14%. The fractions were analyzed by hplc (μ-BONDAPAK C₁₈ reverse phase column eluted with 24% methanol in pH 4.5 0.05M ammonium acetate buffer at 2 ml/min) and those containing the product bulked and freeze dried, 0.20 g, 17%, $\nu_{max}$ (KBr) 1775, 1675, 1610, 1490, 1370, 1270, 1200, 1090, 1012 and 915 cm⁻, δ(D₂O) 0.96, 1.30 and 1.36(6H, 3×s, 2×2CH₃), 2.27(6H, s, 2×OCOCH₃), 4.22(1H, s, 3H), 5.50 and 5.59(2H, 2×s, 5H, CHNH₃⁺), 7.57 and 7.67(2H, 2×s, Ar), 8.10(1H, s, NHCHO).

(c) Sodium 6,β-[D,L-2-(2-chloro-4,5-diacetoxyphenyl)-2-(2,3-dioxo-4-ethylpiperazin-1-ylcarbonylamino)acetamido]-6,α-formamidopenicillanate 2,3-Dioxo-4-ethylpiperazin-1-ylcarbonyl chloride (0.10 g, 0.5 mmole) in acetone (2 ml) was added dropwise to a solution of 6,β-[D,L-2-amino-2-(2-chloro-4,5-diacetoxyphenyl)acetamido]-6,α-formamidopenicillanic acid (0.15 g, 0.27 mmole) in water (5 ml) and acetone (1 ml) maintained at pH 7.0±0.5 with N sodium bicarbonate solution. The solution was stirred for 30 minutes, washed with ether (15 ml) then acidified to pH 2.8 and extracted with ethyl acetate (3×15 ml). The extracts were washed with water (2×10 ml) and brine (10 ml), dried and evaporated to a solid, 0.04 g. This is acetone (4 ml) was treated with 1.85N sodium 2-ethylhexanoate in 4-methylpentan-2-one (0.3 ml), diluted with ether (10 ml) and the precipitate collected, washed with ether and dried in vacuo, 0.039 g, 20%, $\nu_{max}$(KBr) 1770, 1715, 1680, 1610, 1490, 1395, 1370, 1267, 1195, 1140, 1012 and 915 cm⁻¹, δ(D₂O) 1.06, 1.27, 1.31 and 1.41 (6H, 4×s, 2×2CH₃), 1.18(3H, t, J7 Hz, NCH₂CH₃), 2.32(6H, s, 2×OCOCH₃), 3.50(2H, q, J7 Hz, NCH₂CH₃), 3.6–4.1(4H, m, 2×NCH₂), 4.22 and 4.25(1H, 2×s, 3H), 5.57 and 5.59 (1H, 2×s, 5H) 5.92 and 5.93(1H, 2×s, CHNH), 7.47, 7.49 and 7.50(2H, 3×s, Ar), 8.13 and 8.45(1H, 2×s, NHCHO). MIC against *Proteus mirabilis* 889 <0.06 μg/ml.

EXAMPLE 6

(a) D-N-(4-Nitrobenzyloxycarbonyl) 2-chloro-4,5-dihydroxyphenyl glycine

A solution of D-N-(4-nitrobenzyloxycarbonyl) 3,4-dihydroxyphenylglycine (5.43 g, 15 mmole) in glacial acetic acid (30 ml) was treated with surphuryl chloride (1.2 ml, 15 mmole) at room temperature for 30 minutes. diluted with ethyl acetate (250 ml), washed with water (4×200 ml), dried over magnesium sulphte, filtered and evaporated to dryness in vacuo. Crystallised from ether-hexane to yield 2.0 g, 33.6%, $\nu_{max}$ (nujol) 3370, 1725, 1650, 1535, 1510, 1350 and 1060 cm⁻¹, δ[(CD₃)₂CO] 5.20 (2H, s, OCH₂), 5.63(1H, d, J8 Hz, NCHCO₂), 7.17, 7.25(2H, 2×s, Ar), 7.03(1H, d, J8 Hz, NH), 7.73, 7.89(4H, ABq, J9 Hz, 4-NO₂Ph), 8.65(3H, bs, 2×OH, CO₂H).

(b) D-N-(4-Nitrobenzyloxycarbonyl) 2-chloro-4,5-diacetoxyphenylglycine

A solution of D-N-(4-nitrobenzyloxycarbonyl) 2-chloro-4,5 dihydroxyphenylglycine (1.9 g) in 60% aqueous THF (40 ml) at pH 7.5 with saturated sodium carbonate solution was treated with acetic anhydride (1.13 ml) at room temperature. The pH was maintained at 6.5 by additions of saturated sodium carbonate solution. After 45 minutes and 1½ hours further portions of acetic anhydride (0.6 ml) were added. The mixture was washed with ether (2×50 ml), acidified to pH 2.5 with 5N hydrochloric acid, and extracted with ethyl acetate (3×50 ml). The combined extracts were washed with water (3×100 ml), dried over magnesium sulphate, filtered and evaporated to dryness in vacuo to yield 1.6 g, 69.3%, $\nu_{max}$ (CHCl₃) 1780, 1730, 1525, 1495, 1350 and 1190 cm⁻¹, δ[(CD₃)₂CO] 2.20(6H, s, 2×CH₃CO), 5.18(2H, s, OCH₂), 5.82(1H, d, J 8 Hz, CHCO₂), 6.57 (1H, d, J 8 Hz, NH), 7.28(2H, s, Ar), 7.86 and 8.37 (4H, ABq, J8 Hz, 4-NO₂Ph).

(c) Benzyl 6,β-[D-2-(2-chloro-4,5-diacetoxyphenyl)-2-(4-nitrobenzyloxycarbonylamino)acetamido]-6,α-formamidopenicllanate To an ice-cold solution of benzyl 6,β-amino-6,α-formamidopenicillanate (1.97 g) and dicyclohexylcarbodiimide (1.07 g) in dry dichloromethane (40 ml) was added dropwise, over 30 minutes, a solution of D-N-(4-nitrobenzyloxycarbonyl) 2-chloro-4,5-diacetoxyphenylglycine (2.27 g) in dichloromethane (20 ml). The mixture was stirred at 5° for 2 hours and then at room temperature overnight, evaporated to dryness in vacuo, dissolved in acetone, filtered and evaporated to dryness in vacuo. Column chromatography on silica gel eluting with ethyl acetate in cyclohexane, 50% grading to 70%, gave the title compound 1.27 g, 33.2%, $\nu_{max}$ (CHCl$_3$), 1785, 1745, 1700, 1525, 1490, 1350 and 1185 cm$^{-1}$, $\delta$[(CD$_3$)$_2$CO] 1.20 and 1.30 (6H, 2×s, 2×2CH$_3$), 2.27(6H, s, 2×CH$_3$CO), 4.43 (1H, s, 3H), 5.21 (4H, s, 2×OCH$_2$), 5.58(1H, s, 5H), 5.88 (1H, d, J8 Hz, CHCON), 7.15–8.90 (15H, m, Ph, 4-NO$_2$Ph, Ar, 3×NH, CHO).

(d) 6,β-[D-2-amino-(2-chloro-4,5-diacetoxyphenyl)-2 acetamido]-6,α-formamidopenicillanate acid A solution of benzyl 6,β-[D-2-(2-chloro-4,5-diacetoxyphenyl)-2-(4-nitrobenzyloxycarbonylamino)acetamido]-6,α-formamido penicillanate (1.25 g) in 30% aqueous THF (70 ml) was hydrogenated at room temperature and pressure over 10% Pd/C (1.25 g). After 75 minutes the catalyst was changed for fresh (1 g) and hydrogenation continued for 4½ hours. The catalyst was filtered off and the THF evaporated off in vacuo. The solution was washed with ethyl acetate (3×50 ml), filtered through celite and the aqueous freeze dried to yield 0.38 g, 45.5%, $\nu_{max}$ (KBr) 3400(b), 1775, 1680, 1610, 1490, 1375 and 1205 cm$^{-1}$, $\delta$(D$_2$O) 0.98 and 1.30(6H, 2×s, 2×2CH$_3$), 2.28(6H, s, 2×CH$_3$CO), 4.12(1H, s, 3H), 5.53(2H, s, 5H, CHCON), 7.49 and 7.61(2H, 2×s, Ar), 8.03(1H, s, CHO).

(e) Sodium 6,β-[D-2-(2-chloro-4,5-diacetoxyphenyl)-2-(2,3-dioxo-4-ethylpiperazin-1-ylcarbonylamino acetamido]-6,α-formamidopenicillanate To a solution of 6,β-[D-2-amino-2-(2-chloro-4,5-diacetoxyphenyl)acetamido]-6,β-formamidopenicillanate (0.38 g, 0.7 mmole) at room temperature in water (5 ml) at pH 7 with 1N sodium bicarbonate solution was added dropwise to the solution of 2,3-dioxo-4-ethylpiperazin-1-ylcarbonyl chloride (0.168 g, 0.82 mmole) in acetone (3 ml). The pH was maintained at 6.8–7.1 by additions of 1N sodium bicarbonate solution. After 30 minutes the mixture was washed with ether (10 ml). The pH of the aqueous was adjusted to 2.8 with 5N hydrochloric acid and extracted with ethyl acetate (3×10 ml). The combined extracts were washed with water (3×20 ml), dried over magnesium sulphate, filtered and evaporated to dryness in vacuo, dissolved in acetone (5 ml) and 1.85N sodium 2-ethylhexanoate in 4-methylpentan-2-one (0.23 ml) added. The precipitate was filtered off, washed with acetone and ether to yield 0.12 g, 24.1%, $\nu_{max}$ (KBr) 3400(br), 1775, 1710, 1680, 1610, 1490, 1370 and 1200 cm$^{-1}$, $\delta$(D$_2$O) 1.07 and 1.32 (6H, 2×s, 2×2CH$_3$), 1.18 (3H, t, J7Hz, CH$_3$CH$_2$), 2.33(6H, s, 2×CH$_3$CO), 3.50(2H, q, J7 Hz, CH$_3$CH$_2$—), 3.67 and 3.96(4H, 2×n, NCH$_2$CH$_2$N), 4.23 (1H, s, 3H), 5.59(1H, s, 5H), 5.93(1H, s, CHCON), 7.47 and 7.49(2H, 2×s, Ar), 8.13(1H, s, CHO). MIC against *Proteus mirabilis* 889 <0.06 μg/ml.

EXAMPLE 7

(a) N-(4-Nitrobenzyloxycarbonyl)-4,5-dihydroxy-2-fluorophenylglycine

4-Nitrobenzylcarbamate (5.25 g, 27 mmole) and glyoxylic acid hydrate (3.03 g, 33 mmole) in THF(75 ml) were heated under reflux for 3 hours, cooled to room temperature, covered with an atmosphere of argon then treated with boron trifluoride etherate (5.4 ml) followed by 4-fluorocatechol (5.14 g, 40 mmole) in THF(20 ml). The solution was stirred for two hours then poured onto ice, saturated sodium carbonate and ethyl acetate. The aqueous layer was collected washed with ethyl acetate (100 ml), acidified to pH 2.5 and extracted with ethyl acetate (3×75 ml). The extracts were washed with water (2×100 ml) and brine (50 ml), dried and evaporated to a foam, 8.25 g, 80%, $\delta$[(CD$_3$)$_2$CO] 5.17 (2H, s, OCH$_2$), 5.42(1H, d, J8 Hz, CHNH), 5.6–6.8 (4H, broad, NH, 2×OH, CO$_2$H), 6.53(1H, d, JFH 11 Hz, Ar 3-H), 6.78(1H, d, JFH 6.5 Hz, Ar 6-H), 7.51 and 8.06 (4H, ABq, J8 Hz, 4-NO$_2$ Ph).

(b) N-(4-Nitrobenzyloxycarbonyl) 4,5-diacetoxy-2-fluorophenylglycine

Acetic anhydride (4.3 ml) was added to a solution of N-(4-nitrobenzyloxycarbonyl) 4,5-dihydroxy-2-fluorophenylglycine (8.25 g), triethylamine (9.1 ml) and 4-dimethylaminopyridine (0.05 g) in dichloromethane (100 ml). The solution was stirred for one hour, washed with dilute hydrochloric acid (50 ml) and water (2×50 ml), dried and evaporated to a foam, 8.00 g, 80%, $\nu_{max}$ (CH$_2$CL$_2$) 1770, 1725, 1520, 1500, 1345, 1202 and 890 cm$^{-1}$, $\delta$[(CD$_3$)CO] 2.23(6H, s, 2×OCOCH$_3$), 5.20 (2H, s, OCH$_2$), 5.60(1H, d, J8 Hz, CHNH), 6.7–7.5 (2H, m, CO$_2$H, NH), 7.10 (1H, d, JFH 10Hz, Ar 3-H), 7.31 (1H, d, JFH 7 Hz, Ar 6-H), 7.52 and 8.10 (4H, ABq, J 9 Hz, 4-NO$_2$Ph).

(c) Benzyl 6,β-[D,L-2-(4,5-diacetoxy-2-fluorophenyl)-2-(4-nitrobenzyloxycarbonyl amino)acetamido]penicllanate Oxalyl chloride (1 ml) was added to N-(4-nitrobenzyl-oxycarbonyl)-4,5-diacetoxy-2-fluorophenylglycine (2.32 g, 5 mmole) and DMF (1 drop) in dichloromethane (20 ml) stirred for one hour and evaporated to a foam in vacuo. This acid chloride was redissolved in dichloromethane (25 ml) and added dropwise to benzyl 6,β-aminopenicillanate (1.68 g, 5.5 mmole) and pyridine (0.5 ml) in dichloromethane (15 ml) cooled in an ice bath. The reaction was stirred for one hour, washed with dilute hydrochloric acid (25 ml) and water (2×25 ml) dried and evaporated to a foam which was chromatographed on silica gel eluting with 2% methanol in dichloromethane, 2.54 g, 68%, $\delta$(CDCl$_3$), 1.37, 1.39, 1.46 and 1.50 (6H, 4×s, 2×2CH$_3$), 2.27 and 2.29 (6H, 2×s, 2×OCOCH$_3$), 4.45 and 4.47 (1H, 2×s, 3H), 5.16, 5.17 and 5.19 (4H, 3×s, 2×OCH$_2$), 5.4–5.6 (3H, m, 5 and 6H, CHNH), 6.12 and 6.24(1H, 2×d, J7.5 Hz, NH), 6.60 and 6.64(1H, 2×d, J7 Hz, NH), 7.05(1H, d, JFH 10 Hz, Ar 3-H), 7.3–7.45 (6H, m, Ph and Ar 6-H), 7.50 and 8.20(4H, ABq, J7.5Hz, 4-NO$_2$Ph).

(d) 6,β-[D,L-2-Amino-2-(4,5-diacetoxy-2-fluorophenyl) acetamido]penicillanic acid Benzyl 6,β-[D,L-2-(4,5-diacetoxy-2-fluorophenyl)-2-(4-nitrobenzyloxycarbonylamino)acetamido]penicillanate (2.50 g) in THF(40 ml) was diluted with water until just not cloudy then hydrogenated in the presence of 10% palladium on carbon (2.5 g) for 1.5 hours. The catalyst was replaced, hydrogenation continued for a further 0.5 hours and filtered. The filtrate was concentrated in vacuo, the aqueous residue adjusted to pH 5.5, washed with ethyl acetate (2×25 ml) and ether (25 ml)

and further concentrated to ca 5 ml in vacuo. This solution was chromatographed on HP20SS resin eluting with acetone in water, 0% grading to 10%. The fractions were analysed by hplc (μ-BONDAPAK C$_{18}$ reverse phase column eluted with 32% methanol in pH 4.5 0.05M ammonium acetate buffer at 2 ml/min) and those containing the product were bulked and freeze dried, 0.43 g, 26%, ν$_{max}$ (KBr) 1775, 1690, 1620, 1305, 1420, 1372, 1310, 1205, 1160, 1092 1010 and 915 cm$^{-1}$, δ(D$_2$O) 1.41, 1.46 and 1.50(6H, 3×s, 2×2CH$_3$), 2.39(6H, s, 2×OCOCH$_3$), 4.22 and 4.26(1H, 2×s, 3H), 5.3–5.7(3H, m, 5 and 6H, CH NH$_3$+), 7.35(1H, d, JFH 10 Hz, Ar 3-H), 7.47 (1H, d, JFH 6 Hz, Ar 6-H). Hplc analysis (μ-BONDAPAK C$_{18}$ reverse phase column eluted with 32% methanol in pH 4.5 0.05M ammonium acetate buffer at 2 ml/min) showed a 2:1 mixture of D:L diasteroisomers.

(e) Sodium 6,β-[D,L-2-(4,5-diacetoxy-2-fluorophenyl)-2-(2,3-dioxo-4-ethylpiperazin-1-ylcarbonylamino)acetamido]-penicillanate 2,3-Dioxo-4-ethylpiperazin-1-ylcarbonyl chloride (0.18 g, 0.87 mmole) in acetone (3 ml) was added to a solution of 6,β-[D,L-2-amino-2-(4,5-diacetoxy-2-fluorophenyl)acetam ido]penicillanic acid (0.38 g, 0.79 mmole) in water (15 ml) and acetone (2 ml) maintained at pH 6.2±0.25 with 0.5N sodium bicarbonate solution. The reaction was stirred for 15 minutes, washed with ether (25 ml), acidified to pH 2.5 and extracted with ethyl acetate (3×15 ml). The extracts were washed with water (2×15 ml) and brine (15 ml), dried and evaporated to a foam, 0.15 g. This in acetone (10 ml) was treated with 1.85N sodium 2-ethylhexanoate in 4-methylpentan-2-one (0.42 ml), diluted with ether (10 ml) and the precipitated sodium salt collected, washed with ether and dried, 0.48 g, 91%, ν$_{max}$ (KBr) 1770, 1715, 1680, 1610, 1504, 1462, 1400, 1370, 1320, 1200, 1105, 1012 and 920 cm$^{-1}$. δ(D$_2$O) 1.20(3H, t, J6 Hz, NCH$_2$CH$_3$), 1.40, 1.43 and 1.50(6H, 3×s, 2×2CH$_3$), 2.35(6H, s, 2×OCOCH$_3$), 3.52(2H, q, J6 Hz, NCH$_2$CH$_3$), 3.6–4.1(4H, m, 2×NCH$_2$), 4.19(D) and 4.23(L) (1H, 2×s, 3H), 5.38 and 5.54 (D), 5.43 and 5.59(L) (2H, 2×ABq, J 3.9 Hz, 5 and 6H), 5.80(D) and 5.82(L) (1H, 2×s, CHNH), 7.25(L) and 7.255(D) (1H, d, JFH 10.2 Hz, Ar 3-H), 7.40(D) and 7.43(L) (1H, d, 6.9 Hz, Ar 6-H). MIC against *Klebsiella aerogenes* A 0.5 μg/ml.

EXAMPLE 8

(a) Benzyl 6,β-[D,L-2-(4,5-diacetoxy-2-fluorophenyl)-2-(4-nitrobenzyloxycarbonylamino)acetamido]-6,α-formamidopenicillanate The title compound was prepared from N-(4-nitrobenzyloxycarbonyl)4,5-diacetoxy-2-fluorophenylglycine (3.48 g 7.5 mmole) and benzyl 6,β-amino-6,α-formamidopenicillanate (2.10 g, 6 mmole) using the method described in example 7c, 1.63 g, 34%, δ[(CD$_3$)$_2$CO] 1.0–1.5(6H, m, 2×2CH$_3$), 2.22 (6H, s, 2×OCOCH$_3$), 4.42 and 4.48(1H, 2×s, 3H), 5.13(4H, s, 2×OCH$_2$), 5.60(1H, s, 5H), 5.77 (1H, d, J8 Hz, CHNH), 7.03(1H, d, JFH 10 Hz, Ar 3-H), 7.28(5H, s, Ph), 7.3–9.0 (8H, m, 4-NO$_2$ Ph, Ar 6-H, NHCHO, CONH).

(b) 6,β-[D-2-Amino-2-(4,5-diacetoxy-2-fluorophenyl)acetamido]-6,α-formamidopenicillanic acid Benzyl 6,β[D,L-2-(4,5-diacetoxy-2-fluorophenyl)-2-(4-nitrobenzyloxycarbonylamino)acetamido]-6,α-formamidopenicillanate (1.60 g), in THF(30 ml) was diluted with water until just not cloudy then hydrogenated in the presence of 10% palladium on carbon (1.6 g) for 2.5 hours, filtered and the filtrate concentrated in vacuo. The aqueous residue was adjusted to pH 5, washed with ethyl acetate (2×25 ml) and freeze dried, 0.69 g. This in water (5 ml) was chromatographed on HP2OSS resin eluting with acetone in water, 0% grading to 8%. The fractions were analysed by hplc (μ-BONDAPAK C$_{18}$ reverse phase column eluted with 24% methanol in pH 4.5 0.05M ammonium acetate buffer at 2 ml/min) and the fractions containing the produce were bulked and freeze dried, 0.22 g, ν$_{max}$ (KBr) 1770, 1685, 1605, 1504, 1372, 1211, 1162, 1098, 1014 and 924 cm$^{-1}$, δ(D$_2$O) 0.97 and 1.33 (6H, 2×s, 2×2CH$_3$), 2.36 and 2.37(6H, 2×s, 2×OCOCH$_3$), 4.22(1H, s, 3H), 5.45 and 5.65 (2H, 2×s, 5H and CHNH$_3$+), 7.35(1H, d, JFH 10.1 Hz, Ar 3-H), 7.62(1H, d, JFH 6.8Hz, Ar 6.H), 8.15(1H, s, NHCHO).

(c) Sodium 6,β-[D-2-(4,5-diacetoxy-2-fluorophenyl)-2-(2,3-dioxo-4-ethylpiperazin-1-ylcarbonylamino) acetamido]-6,α-formamidopenicillanate 2,3-Dioxo-4-ethylpiperazin-1-ylcarbonyl chloride (0.11 g, 0.54 mmole) in acetone (2 ml) was added dropwise to 6,β-[D-2-amino-2-(4,5-diacetoxy-2-fluorophenyl)acetamido]-6,α-formamidopenicillanic acid (0.19 g) in water (8 ml) and acetone (2 ml) maintained at pH 6.25±0.25 with 0.5N sodium bicarbonate solution. The solution was stirred for 30 minutes, washed with ether (15 ml), acidified to pH 2.5 extracted with ethyl acetate (3×10 ml). The extracts were washed with water (2×10 ml) and brine (10 ml) dried and evaporated to a foam, 0.17 g. This in acetone (5 ml) was treated with 1.85N sodium 2-ethylhexanoate in 4-methylpentan-2-one (0.13 ml) and the precipitate collected, washed with acetone and ether and dried in vacuo, 0.16 g, ν$_{max}$ (KBr) 1770, 1710, 1682, 1610, 1502, 1395, 1370, 1203, 1106 and 1013 cm$^{-1}$, δ(D$_2$O) 0.98 and 1.31(6H, 2×s, 2×2CH$_3$), 1.19(3H, t, J7.1 Hz, NCH$_2$CH$_3$), 2.33(6H, s, 2×OCOCH$_3$), 3.51(2H, q, J7.1 Hz, NCH$_2$CH$_3$), 3.68 and 3.97 (4H, 2×m, 2×NCH$_2$), 4.21(1H, s, 3H), 5.61(1H, s, 5H), 5.77(1H, s, CHNH), 7.25(1H, d, JFH 9.9 Hz, Ar 3-H), 7.44(1H, d, JFH 6.9 HZ, Ar 6-H), 8.13(1H, s, NHCHO). MIC against *Proteus mirabilis* 889 <0.06 μg/ml.

EXAMPLE 9

(a) Benzyl 6,β-[D-2-(2-chloro-4,5-diacetoxyphenyl)-2-(4-nitrobenzyloxycarbonylamino)acetamido]penicillante A solution of D-N-(4-nitrobenzyloxycarbonyl)-2-chloro-4,5-diacetoxyphenylglycine (2.4 g, 5 mmol) in dry dichloromethane (20 ml) at room temperature was treated with oxalyl chloride (1 ml) and dry DMF (1 drop), after 1 hour the solution was evaporated to dryness in vacuo. This acid chloride was redissolved in dichloromethane (20 ml) and added dropwise to benzyl 6,β-aminopenicillanate (1.83 g, 6 mmol) and pyridine (0.4 ml) in dichloromethane (10 ml) cooled in an ice-bath. The reaction was stirred for 1 hour, washed with 1N hydrochloric acid (30 ml), water (3×30 ml), dried and evaporated in vacuo. The residue was chromatographed on silica gel eluting with ethylacetate in cyclohexane, 20% grading to 50%, 1.4 g, 36.5%, δ[(CD$_3$)$_2$CO] 1.34, 1.47(6H, 2×s, 2×2CH$_3$), 2.21(6H, s, 2×OCOCH$_3$), 4.46(1H, s, 3H), 5.22(4H, s, 2×OCH$_2$), 5.5–6.0(3H, m, 5 and 6H, CHNH), 7.3–8.35(13H, Ph, Ar, 4-NO$_2$Ph, 2×NH).

(b)
6,β-[D-2-Amino-2-(2-chloro-4,5-diacetoxyphenyl)acetamido]penicillanic acid Benzyl 6,β-[D-2-(2-chloro-4,5-diacetoxyphenyl)-2-(4-nitrobenzyloxycarbonylamino)acetamido]penicillanate (1.4 g) in THF (40 ml) and water (10 ml) was hydrogenated in the presence of 10% palladium on carbon (1.4 g) for one hour. The catalyst was replaced, hydrogenation continued for a further one hour and filtered. The solution was washed with ethyl acetate (3×10 ml) then ether (3×10 ml) and freeze dried. The product was isolated by chromatography on HP2OSS resin eluting with water grading to 10% acetone in water, 0.15 g, 16.5%, ν$_{max}$ (KBr) 3397, 1774, 1691, 1610, 1206, 1013 and 916 cm$^{-1}$, δ(D$_2$O) 1.38, 1.41(6H, 2×s, 2×2CH$_3$), 2.32(6H, s, 2×OCOCH$_3$), 4.12, (1H, s, 3H), 5.35–5.65(3H, m, 5 and 6H, CHNH), 7.44, 7.57(2H, 2×s, Ar).

(c) Sodium 6,β-[D-2-(2-chloro-4,5-diacetoxyphenyl)-2-(2,3-dioxo-4-ethylpiperazin-1-ylcarbonylamino)acetamido]penicillanate 2,3-Dioxo-4-ethylpiperazin-1-ylcarbonyl chloride (60 mg) in acetone (2 ml) was added to a solution of 6,β-[D-2-amino-2-(2-chloro-4,5-diacetoxyphenyl)acetamido]penicillanic acid (117 mg) in water (4 ml) and acetone (1 ml) maintained at pH 7 with saturated sodium carbonate solution. The reaction was stirred for 30 minutes, washed with ethyl acetate (2×10 ml), acidified to pH 2.2 and extracted with ethyl acetate (3×5 ml). The extracts were washed with water (4×10 ml), dried and evaporated in vacuo. This in acetone (2 ml) was treated with 1.85N sodium 2-ethylhexanoate in 4-methylpentan-2-one (0.08 ml). The precipitated salt was collected, washed with ether and dried, 60 mg, 38%, ν$_{max}$ (KBr) 3402, 1772, 1714, 1683, 1609 1507, 1397, 1369, 1204 cm$^{-1}$, δ(D$_2$O) 1.15(3H, t, J6 Hz, NCH$_2$CH$_3$), 1.41(6H, s, 2×2CH$_3$), 2,29(6H, s, 2×OCOCH$_3$), 3.45(2H, q, J6 Hz, NCH$_2$CH$_3$), 3.50–4.05(4H, m, 2×NCH$_2$), 4.15(1H, s, 3H), 5.39, 5.49(2H, ABq, J4 Hz, 5 and 6H), 5.84(1H, s, CHNH), 7.38, 7.41(2H, 2×s, Ar) MIC against *Klebsiella aerogenes* A 0.25 μg/ml.

EXAMPLE 10

(a)
N-(2,3-Dioxo-4-ethylpiperazin-1-yl-carbonyl)-2-(2-bromo-4,5-dihydroxyphenyl)glycine 4-Bromocatechol (4.77 g, 25.2 mmole) was added to an ice bath cooled suspension of N-(2,3-dioxo-4-ethylpiperazin-1-yl-carbonyl)-2-hydroxyglycine (2.59 g. 10 mmole) in glacial acetic acid (9 ml) and concentrated sulphuric acid (1 ml). The mixture was stirred for 18 hours then poured onto a mixture of ice, saturated sodium carbonate and ethyl acetate and adjusted to pH7 with sodium carbonate. The aqueous layer was collected, washed with ethyl acetate (50 ml), acidified to pH1 and extracted with ethyl acetate (3×50 ml). The extracts were dried and evaporated in vacuo to a buff solid, 2.4 g, 79%, δ[(CD$_3$)$_2$CO]1.13(3H, t, J7 Hz, CH$_2$CH$_3$), 3.57(2H, q, J7 Hz, CH$_2$CH$_3$), 3.5–4.3(4H, m, 2×NCH$_2$), 5.3–7.6(3H, broad, 2×OH, CO$_2$H), 5.73(1H, d, J6.5 Hz, CHNH), 6.87 and 7.03 (2H, 2×s, Ar), 9.73(1H, d, J6.5 Hz, CHNH).

(b)
N-(2,3-Dioxo-4-ethylpiperazin-1-yl-carbonyl)-2-(2-bromo-4,5-diacetoxyphenyl)glycine Acetic anhydride (1.62 ml, 17.1 mmole) was added to a solution of N-(2,3-dioxo-4-ethylpiperazin-1-yl-carbonyl)-2-(2-bromo-4,5-dihydroxyphenyl)glycine (3.4 g, 7.9 mmole), 4-dimethylaminopyridine (97 mg, 0.79 mmole) and triethylamine (3.31 ml, 23.7 mmole) in dichloromethane (25 ml). The mixture was stirred for 3.5 hours then washed with 5N hydrochloric acid (2×10 ml) and water (2×20 ml), dried and evaporated in vacuo to an off white solid, 3.4 g, 83.7% δ[(CD$_3$)$_2$CO]1.14(3H, t, 7 Hz, CH$_2$CH$_3$), 2.23(6H, s, 2×OCOCH$_3$), 3.46(2H, q, J7 Hz, CH$_2$CH$_3$), 3.5–4.1(4H, m, 2×NCH$_2$), 4.5–6.0(1H, broad, CO$_2$H), 5.87(1H, d, J6.5 Hz, CHNH), 7.22 and 7.56(2H, 2×s, Ar) 10.05(1H, d, J6.5 Hz, CHNH).

(c) Sodium 6,β-[D,L-2-(2-bromo-4,5-diacetoxyphenyl)-2-(2,3-dioxo-4-ethylpiperazin-1-ylcarbonylamino)acetamido]penicillanate N-(2-3-Dioxo-4-ethylpiperazin-1-ylcarbonyl)-2-(2-bromo-4,5-diacetoxyphenyl)glycine (3.35 g, 6.51 mmole) in freshly dried acetone (100 ml) was cooled in an ice bath then treated with triethylamine (0.91 ml, 6.51 mmole) and trimethylacetyl chloride (0.80 ml, 6.51 mmole). The mixture was stirred at ca. 0° for 1.5 hours then filtered into an ice bath cooled solution of 6,β-aminopenicillanic acid (1.407 g, 6.51 mmole) in 50% aqueous acetone (84 ml) containing sodium hydroxide (0.26 g, 6.51 mmole) and sodium bicarbonate (0.55 g, 6.51 mmole). After one hour the mixture was concentrated in vacuo, washed with ether (2×50 ml), acidified to pH 2.5 and extracted with ethyl acetate (2×50 ml). The extracts were washed with water (2×50 ml) and saturated brine (25 ml), dried and evaporated to a foam, 3.17 g. This in acetone (10 ml) was treated with 1.85N sodium 2-ethylhexanoate in 4-methylpentan-2-one (2.8 ml) to precipitate a mixture of sodium salts which were collected, washed with ether and dried, 3.31 g. The title compound was isolated by chromatography on HP2OSS eluting with THF in water, 0% grading to 8%, 0.55 g, 11.5% ν$_{max}$ (KBr) 1772, 1713, 1680, 1609, 1485, 1395, 1369, 1324, 1268, 1202, 1137, 1097, 1013 and 914 cm$^{-1}$, δ(D$_2$O) 1.13(3H, t, J7 Hz, CH$_2$CH$_3$), 1.38 (6H, s, 2×2CH$_3$), 2.27(6H, s, 2×OCOCH$_3$), 3.43 (2H, q, J 7 Hz, CH$_2$CH$_3$), 3.5–4.1(4H, m, 2×NCH$_2$), 4.12(D) and 4.23(L) (1H, 2×s, 3H), 5.3–5.6(2H, m, 5 and 6H), 5.86(1H, s, CHNH), 7.36(L) and 7.38(D) (1H, 2×s, Ar), 7.55(1H, s, Ar). MIC against *Klebsiella aerogenes* A 1.0 μg/ml.

EXAMPLE 11

Sodium 6,β-[D-2-(4,5-dihydroxy-2-fluorophenyl)-2-(2,3-dioxo-4-ethylpiperazin-1-ylcarbonylamino)acetamido]penicillanate Sodium 6,β-[D,L-2-(4,5-diacetoxy-2-fluorophenyl)-2-(2,3-dioxo-4-ethylpiperazin-1-ylcarbonylamino)acetamido]penicillanate (59 mg) in water (2 ml) was adjusted to pH 7 (0.5N NaHCO$_3$), Cirtus acetylesterase suspension (Sigma Chemical Co. Product No. A-4530, 0.4 ml) was added and the mixture maintained at pH 6.5±0.5 for one hour then chromatographed on HP2OSS eluting with acetone in water, 0% grading to 8%, to give the title compound, 18 mg, 35% $\nu_{max}$ (KBr) 1767, 1711, 1675, 1609, 1521, 1459, 1398, 1369, 1324, 1192, 1111 and 953 cm$^{-1}$, δ(D$_2$O) 1.20(3H, t, J7 Hz, CH$_2$CH$_3$), 1.41 and 1.44(6H, 2×s, 2×2CH$_3$), 3.52 (2H, q, J7 Hz, CH$_2$CH$_3$), 3.6–4.15(4H, m, 2×NCH$_2$), 4.21 (1H, s, 3H), 5.39 and 5.51(2H, ABq, J3.5 Hz, 5 and 6H), 5.61(1H, s, CHNH), 6.76(1H, d, J$_{HF}$ 9 Hz, Ar), 6.90 (1H, d, J$_{HF}$ 7 Hz, Ar). MIC against *Klebsiella areogenes* A 1.0 μg/ml.

EXAMPLE 12

(a) D-2-(2-Chloro-4,5-dihydroxyphenyl)glycine

D-2-(2-Chloro-4,5-dihydroxyphenyl)-N-(4-nitrobenzyloxycarbonyl)glycine (9.8 g) in glacial acetic acid (4 ml) and 45% w/v hydrogen bromide in glacial acetic acid (31 ml) was gently warmed to obtain an almost clear solution. After 1 hour at room temperature the clear solution was diluted with water (150 ml), washed with ether (3×100 ml) and adjusted to pH 5 with 40% sodium hydroxide solution. The precipitated solid was collected, washed with water, ether and dried, 3 g, 46.7%, [α]$_D^{20}$ cl in 1.75M HC)—105.4°.

(b) D-2-(2-Chloro-4,5-dihydroxyphenyl)-N-(2,3-dioxo-4-ethylpiperazin-1-ylcarbonyl)glycine D-2-(2-Chloro-4,5-dihydroxyphenyl)glycine (2.97 g) and chlorotrimethylsilane (1 ml) in hexamethyldisilazane (36 ml) were refluxed under an atmosphere of nitrogen for 2 hours, then evaporated in vacuo. The residue was dissolved in THF (20 ml) and cooled in an ice-bath. A solution of 2,3-dioxo-4-ethylpiperazin-1-ylcarbonyl chloride (3.1 g) in THF (20 ml) was added dropwise over 0.5 hours. The mixture was allowed to gain room temperature and stirred for 1 hour, diluted with ethyl acetate (150 ml), butanol (20 ml), water (150 ml) and stirred for a further 20 minutes. The aqueous was discarded and the organic phase washed with water (4×100 ml), dried and evaporated in vacuo 3.7 g, 81% δ[(CD$_3$)$_2$CO]1.15(3H, t, J6 Hz, NCH$_2$CH$_3$), 3.50(2H, q, J6 Hz, NCH$_2$CH$_3$), 3.70, 4.05(4H, 2×m, NCH$_2$CH$_2$N), 5.81 (1H, d, J7 Hz, CHNH), 6.91, 6.94, (2H, 2×s, Ar), 9.80 (1H, d, J7 Hz, CHNH).

(c) D-2-(2-Chloro-4,5-diacetoxyphenyl)-N-(2,3-dioxo-4-ethylpiperazin-1-ylcarbonyl)glycine A solution of D-2-(2-chloro-4,5-dihydroxyphenyl)-N-(2,3-dioxo-4-ethylpiperazin-1-ylcarbonyl)glycine (3.7 g), triethylamine (4 ml), acetic anhydride (2 ml) and 4-dimethylaminopyridine (50 mg) in dry dichloromethane (50 ml) was stirred at room temperature for 1 hour, washed with 1N hydrochloric acid (25 ml) and water (3×50 ml), dried and evaporated in vacuo, 3.85 g, 82.2%, δ[CD$_3$)$_2$CO]1.13 (3H, t, J7 Hz, NCH$_2$CH$_3$), 2.23(6H, s, 2×OCOCH$_3$), 3.51 (2H, q, J7 Hz, NCH$_2$CH$_3$), 3.62, 4.02(4H, 2×m, NCH$_2$CH$_2$N), 5.95(1H, d, J7 Hz, CHNH), 7.42(2H, s, Ar).

(d) Benzyl 6,β-[D-2-(2-chloro-4,5-diacetoxyphenyl)-2-(2,3-dioxo-4-ethylpiperazin-1-ylcarbonylamino)acetamido]-6,α-formamidopenicillanate To an ice cold solution of benzyl 6,β-amino-6,α-formamidopenicillanate (3.49 g) and dicyclohexylcarbodiimide (1.80 g) in dry dichloromethane (20 ml) was added dropwise D-2-(2-chloro-4,5-diacetoxyphenyl)-N-(2,3-dioxo-4-ethylpiperazin-1-ylcarbonyl)glycine (3.85 g) in dry dichloromethane (10 ml). The mixture was stirred at 5° for 48 hours, filtered, evaporated in vacuo and the residue chromatographed on silica eluting with ethyl acetate, 3.4 g, 52%, δ[(CD$_3$)$_2$CO]1.15, 1.26(6H, 2×s, 2×2 CH$_3$), 1.20(3H, t, J7 Hz, NCH$_2$CH$_3$), 2.23(6H, s, 2×OCOCH$_3$), 3.25–4.10(6H, m, NCH$_2$CH$_3$, NCH$_2$CH$_2$N), 4.53(1H, s, 3H), 5.25(2H, s, OCH$_2$), 5.70(1H, s, 5H), 6.10(1H, d, J6 Hz, CHNH), 7.42(5H, s, Ph), 7.52(2H, s, Ar), 8.23 (1H, bs, CHO), 8.42, 8.64(2H, 2×bs, NHCHO, CONH), 10.10(1H, d, J6 Hz, CHNH).

(e) Sodium 6,β-[D-2-(2-chloro-4,5-diacetoxyphenyl)-2-(2,3-dioxo-4-ethylpiperazin-1-ylcarbonylamino)acetamido]-6,α-formamidopenicillanate A solution of benzyl 6,β-[D-2-(2-chloro-4,5-diacetoxyphenyl)-2-(2,3-dioxo-4-ethylpiperazin-1-ylcarbonylamino)-acetamido]-6,α-formamidopenicillanate (3.3 g) in THF (150 ml) was hydrogenated at ambient temperature and pressure over 10% palladium on carbon (3.0 g) for 30 minutes, filtered and evaporated in vacuo. The residue was dissolved in acetone (5 ml) and 1.85N sodium 2-ethylhexanoate in 4-methylpentan-2-one (1.7 ml) added. The solid was precipitated with ether (50 ml), collected, washed with ether and dried, 2.1 g, 71.7%, spectral data as for example 6 (e).

(f) Sodium 6,β-[D-2-(2-chloro-4,5-dihydroxyphenyl)-2-(2,3-dioxo-4-ethyl-piperazin-1-ylcarbonylamino)acetamido]-6,α-formamidopenicillanate Sodium 6,β-[D-2-(2-chloro-4,5-diacetoxyphenyl)-2-(2,3-dioxo-4-ethyl-piperazin-1-yl-carbonylamino)acetamido]-6,α-formamidopenicillanate (0.5 g) in water (2 ml) was adjusted to pH 7 (1N NaHCO$_3$), citrus acetylesterase suspension (Sigma Chemical Co. product No. A-4530, 0.5 ml portions at 0, 30, 60 and 90 minutes) was added and the mixture maintained at pH 6.8±0.2 for two hours. The crude preparation was chromatographed on HP20SS resin eluting with acetone in water, 0% grading to 4%, to give the title compound, 190 mg, 43%, $\nu_{max}$ (KBr) 3263 (b), 1772, 1676, 1609, 1507, 1460, 1395, 1368, 1285 and 900 cm$^{-1}$, δ(D$_2$O) 1.03, 1.33, (6H, 2×s, 2×2 CH$_3$), 1.18, (3H, t, 5 Hz, NCH$_2$CH$_3$), 3.49 (2H, q, J5 Hz, NCH$_2$CH$_3$), 3.66, 3.97 (4H, 2×m, NCH$_2$CH$_2$N), 4.30 (1H, s, 3H), 5.61 (1H, s, 5H), 5.75 (1H, s, CHNH), 6.97, 7.01 (2H, 2×s, Ar) 8.13 (1H, s, CHO).

EXAMPLE 13

7β[D-2-(2-Bromo-4,5-diacetoxyphenyl)-2-[(4-ethyl-2,3-dioxopiperazin-1-yl)carbonylamino]acetamido]-7α-formamidocephalosporanate, sodium salt (a) t-Butyl 7β-[D-2-(2-bromo-4,5-diacetoxyphenyl)-2-[(4-ethyl-2,3-dioxopiperazin-1-yl)carbonylamino]acetamido]-7α-formamidocephalosporanate Freshly prepared 2-(2-bromo-4,5-diacetoxyphenyl)-2-[(4-ethyl-2,3-dioxopiperazin-1-yl)carbonylamino]acetyl chloride, generated by treatment of the corresponding acid (108 mg, 0.210 mmol) with oxalyl chloride (53.4 mg, 0.420 mmol) in dry dichloromethane (5 ml) and N,N-dimethylformamide (1/5 drop) for 50 min, was taken up in dry dichloromethane and added to a stirred solution of t-butyl 7β-amino-7α-formamidopcephalosporanate (66 mg, 0.178 mmol) in dry dichloromethane (3 ml), followed by pyridine (14 mg, 0.178 mmol). After 30 mins the mixture was diluted with dichloromethane and washed successively with dilute aqueous sodium hydrogen carbonate, dilute hydrochloric acid, and saturated brine, dried (MgSO$_4$), and evaporated. The residue was chromatographed on silica gel to give the title compound (35 mg) as a pale solid; $\nu_{max}$ (CHCl$_3$) 3270, 2980, 1785, 1740, 1715, and 1690 cm$^{-1}$, δ[(CD$_3$)$_2$CO] inter alia 1.18 (3H, t, J 7 Hz, N.CH$_2$CH$_3$), 1.54 (9H, s, CMe$_3$), 2.0–2.1 (3H, CH$_2$OCOCH$_3$, obscured by solvent), 2.28 and 2.30 (each 3H, s, 2×O-COCH$_3$), 3.20 (1H, J17 Hz, high-field half of 2-CH$_2$ ABq), 3.4–3.6 [together 3H, m, N.CH$_2$ CH$_3$ and low-field half of 2-CH$_2$ ABq, q (J7 Hz) centered at 3.52 discerneable], 3.6–3.8 and 3.95–4.15 (each 2H, m, N.CH$_2$.CH$_2$. N), 4.74 and 5.05 (2H, J 14 Hz, 3-CH$_2$ OAc) 5.20 (1H, s, 6-H), 6.05 (1H, d, J7 Hz, NH.CH.CO), 7.46 and 7.58 (each 1H, s, aromatics), 8.21 and 8.57 (together 1H, each s, NH.CHO, major and minor rotamer respectively), 8.30 br, 8.40 br, 8.47 br, and 8.80 br (together 2H, CO.NH.C and NH.CHO), 9.97 (1H, d, J 7 Hz, CH.NH.CO). (Addition of D$_2$O caused the signals at 8.30, 8.40, 8.47, 8.80 and 9.97 to disappear whilst that at 6.05 collapsed to a s).

(b) 7β[D-2-(2-Bromo-4,5-diacetoxyphenyl)-2-[(4-ethyl-2,3-dioxopiperazin-1-yl)carbonylamino]acetamido]-7α-formamidocephalosporanate, sodium salt t-Butyl 7β[D-2-(2-bromo-4,5-diacetoxyphenyl)-2-[(4-ethyl-2,3-dioxopiperazin-1-yl)carbonylamino]acetamido]-7α-formamidocephalosporanate (32 mg) was dissolved in trifluoroacetic acid (2 ml) and after 15 min at room temperature, the solvent removed in vacuo. The residue was taken up in dilute aqueous sodium hydrogen carbonate, pH adjusted to 6.8 and solution chromatographed on Diaion HP20SS. The relevant fractions were lyophilised to afford the title compound (12 mg) as a white solid, $\nu_{max}$ (KBr) 3290, 2925, 2855, 1770, 1690, 1610, 1515, 1395, 1370 and 1200 cm$^{-1}$, δ(D$_2$O) inter alia 1.18 (3H, t, J 7 Hz, N.CH$_2$CH$_3$), 2.09 (3H, s, CH$_2$OCOCH$_3$), 2.34 and 2.35 (each 3H, s, 2×OCOCH$_3$), 3.15 (1H, J 17 Hz, high-field half of 2-CH$_2$S ABq), 3.4–3.6 (together 3H, m, N.CH$_2$.CH$_3$ and low-field half of 2-CH$_2$S ABq), 3.6–3.8 and 3.9–4.1 (each 2H, m, N.CH$_2$.CH$_2$.N), 4.6–4.9 (2H, 3-CH$_2$ OAc, obscured by solvent), 5.30 (1H, s, 6-H), 5.95 (1H, s, NH.CH.CO), 7.47 and 7.67 (each 1H, 2×s, aromatics) and 8.15 and 8.49 (together 1H, each s, NH.CHO. major and minor rotamer respectively). MIC (μg/ml) against *P. mirabilis* 899 is 0.25

EXAMPLE 14

7β-[D-2-(2-Chloro-4,5-diacetoxyphenyl)-2-[(4-ethyl-2,3-dioxopiperazin-1-yl)carbonylamino]acetamido]-7α-formamidocephalosporanate, sodium salt (a) t-Butyl 7β[D-2-(2-Chloro-4,5-diacetoxyphenyl)-2-[(4-ethyl-2,3-dioxopiperazin-1-yl)carbonylamino]acetamido]-7α-formamidocephalosporanate To a stirred solution of t-butyl 7α-amino-7β-formamidocephalosporanate (242 mg, 0.652 mmol) and dicyclohexylcarbodiimide (161 mg, 0.783 mmol) in dry tetrahydrofuran (10 ml) under argon was added a solution of 2(2-chloro-4,5-diacetoxyphenyl)-2-[(4-ethyl-2,3-dioxopiperazin-1-yl)carbonylamino]acetic acid in dry tetrahydrofuran (10 ml) over 30 min. The resulting mixture was stirred for 20 h and then filtered. The filtrate was evaporated, and the residue dissolved in ethyl acetate, washed successively with dilute aqueous sodium hydrogen carbonate, dilute hydrochloric acid and saturated brine, dried (MgSO$_4$) and evaporated. The residue was chromatographed on silica gel to give the title compound (117 mg); $\nu_{max}$ (CHCl$_3$) 3270, 1785, 1720, 1715 and 1695 cm$^{-1}$, δ(CDCl$_3$) inter alia (major rotamer only) 1.23 (3H, t, J 7 Hz, N.CH$_2$.CH$_3$), 1.55 (9H, s, CMe$_2$), 2.08 (3H, s, CH$_2$OCOCH$_3$), 2.27 and 2.29 (each 3H, s, 2×OCOCH$_3$), 2.95 and 3.30 (2H, ABq, J 16.5 Hz, 2-CH$_2$), 3.56 (2H, q, J 7 Hz, N.CH$_2$.CH$_3$), 3.6–4.2 (4H, m, N.CH$_2$.CH$_2$.N), 4.80 and 5.09 (2H, ABq, J 13 Hz, CH$_2$OCOCH$_3$), 5.12 (1H, s, 6-H), 6.00 (1H, d, J 7 Hz, NH.CH.CO), 7.27 and 7.34 (2H, each s, aromatics), 7.86 br and 7.91 br (each 1H, s, 2×amide NH), 8.18 (1H, s, NH.CHO), and 10.09 (1H, d, J 7 Hz, CH.NH.CO.). (Irradiation at 10.09 caused the signal at 6.00 to collapse into a s). Also isolated from the reaction was t-butyl 7β-[2-L-(2-chloro-4,5-diacetoxyphenyl)-2-[(4-ethyl-2,3-dioxopiperazin-1-yl)carbonylamino]acetamido]-7α-formamidocephalosporanate (100 mg).

(b) 7β-[D-2-(2-chloro-4,5-diacetoxyphenyl)-2-[(4-ethyl-2,3-dioxopiperazin-1-yl)carbonylamino]acetamido]-7α-formamidocephalosporanate, sodium salt t-Butyl 7β-[2-D-(2-chloro-4,5-diacetoxyphenyl)-2-[4-ethyl-2,3-dioxopiperazin-1-yl)carbonylamino]acetamido]-7α-formamidocephalosporanate (107 mg) was dissolved in trifluoroacetic acid (5 ml) and the resulting solution allowed to stand at room temperature. After 15 min the solvent was removed in vacuo and the residue taken up in saturated aqueous sodium hydrogen carbonate. The pH was adjusted to 6.8 and the solution chromatographed on Diaion HP20SS and the relevant fractions lyophilised to give the title compound (53 mg) as a white solid, $\nu_{max}$ (H$_2$O) 255 nm (E$_m$12000), $\nu_{max}$ (KBr) 3400, 3000, 2940, 1770, 1680, 1610, 1490, 1395 and 1200 cm$^{-1}$, δ(D$_2$O) 1.19 (3H, t, J 7 Hz, N.CH$_2$.CH$_3$), 2.12 (3H, s, CH$_2$OCOCH$_3$), 2.34 (6H, s, 2×OCOCH$_3$), 3.12 and 3.16 [together 1H, each d (J 17 Hz), high-field half of 2-CH$_2$ ABq, major and minor rotamer respectively], 3,4–3.6 (3H, m, N.CH$_2$.CH$_3$ and low-field half of 2-CH$_2$ ABq), 3.6–3.75 and 3.9–4.1 (each 2H, m, N.CH$_2$.CH$_2$.N), 4.6–4.9 (2H, 3-CH$_2$OCOCH$_3$, partially obscured by HOD), 5.27 and 5.29 (together 1H, each s, 6-H, minor and major rotamer respectively), 5.93 and 5.95 (together 1H, each s, NH.CH.CO, minor and major rotamer respectively), 7.48 (2H, s, aromatics), and 8.15 and 8.48 (together 1H, each s, NH.CHO, major and minor rotamer respectively).

MIC (μg/ml) against P.mirabilis 889 is <0.06.

EXAMPLE 15

7β-[D-2-(2-Chloro-4,5-diacetoxyphenyl)-2-[(4-ethyl-2,3-dioxopiperazin-1-yl)carbonylamino]acetamido]-7α-formamido-3[(1-methyl-1H-tetrazol-5-yl)thiomethyl]-ceph-3-em-4-carboxylic acid, sodium salt (a) Diphenylmethyl 7β-[D-2-(2-chloro-4,5-diacetoxyphenyl)-2-[(4-ethyl-2,3-dioxopiperazin-1-yl)carbonylamino]acetamido]-7α-formamido-3[(1-methyl-1H-tetrazol-5-yl)thiomethyl]ceph-3-em-4-carboxylate Freshly prepared 2-(2-chloro-4,5-diacetoxyphenyl)-2-[(4-ethyl-2,3-dioxopiperazin-1-yl)carbonylamino]acetyl chloride, generated by treatment of the corresponding acid (105 mg, 0.223 mmol) with oxalyl chloride (56.8 mg, 0.447 mmol) in dry dichloromethane (2 ml) containing N,N-dimethylformamide (1/5 drop) for 90 min, was taken up in dry dichloromethane (3 ml) and added to a stirred solution of diphenylmethyl 7β-amino-7α-formamido-3[(1-methyl-1H-tetrazol-5-yl)thiomethyl]-ceph-3-em-4-carboxylate (80 mg, 0.149 mmol), followed by pyridine (11.8 mg, 0.149 mmol). After 30 min the mixture was diluted with dichloromethane and washed successively with dilute aqeous sodium hydrogen carbonate, dilute hydrochloric acid, and saturated brine, dried (MgSO₄) and evaporated. The residue was chromatographed on silica gel to give the title compound (91 mg) as a pale glass; δ[(CD₃)₂CO] inter alia 1.18 (3H, t, J 7 Hz, N.CH₂.CH ₃), 2.28 and 2.29 (each 3H, s, 2×OCOCH₃), 3.27 [1H, d, J 16 Hz, high-field half of 2-CH₂ ABq] 3.4–3.6 (3H, m, N.CH₂.CH₃ and low-field half of 2-CH₂), 3.6–3.8 and 4.0–4.15 (each 2H, m, N.CH₂.CH₂.N), 3.96 (3H, s, N.CH₃), 4.29 and 4.64 (2H, ABq, J 14 Hz, 3-CH₂S), 5.27 (1H, s, 6-H), 6.09 (1H, d, J 8 Hz, NH.CH.CO), 6.92 (1H, s, CH.Ph₂), 7.2–7.7 (12H, m, aromatics), 8.28 and 8.57 (together 1H, each s, NH.CHO), 8.51 br and 8.54 br (each 1H, s, 2×amide NH), and 10.03 (1H, d, J 8 Hz, CH.NH.CO). (Addition of D₂O caused the signals at 10.03, 8.54 and 8.51 to disappear whilst the signal at 6.09 collapsed to a s).

(b) 7β-[D-2-(2-Chloro-4,5-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid, sodium salt Diphenylmethyl 7β[2-D-(2-chloro-4,5-diacetoxyphenyl)-2[(4-ethyl-2,3-dioxopiperazin-1-yl)carbonylamino]acetamido]-7α-formamido-3[1-methyl-1H-tetrazol-5-yl)thiomethyl]ceph-3-em-4-carboxylate (91 mg) was dissolved in trifluoroacetic acid and the resulting solution allowed to stand at room temperature. After 15 minutes the solvent was removed in vacuo and the residue taken up in saturated aqueous sodium hydrogen carbonate. The pH was adjusted to 6.8 and the solution chromatographed on Diaion HP20SS and the relevant fractions lyophilysed to give the title compound (22 mg) as a white solid, λ$_{max}$. (H₂O) 262 nm (ε$_m$12,700), ν$_{max}$. (KBr) 3440, 3100, 3000, 1775, 1680, 1610, 1490, 1395, 1370, 1280, and 1200 cm⁻¹, δ(D₂O) inter alia 1.18 (3H, t, J 7.5 Hz, NCH₂.CH₃), 2.31 and 2.33 (each 3H, s, 2×OCOCH₃), 3.14 [1H, high-field half of 2-CH₂ ABq (J17 Hz)], 3.4–3.6 (together 3H, m, N.CH₂.CH₃ and low-field half of 2-CH₂), 3.6–3.8 (2H, m, N.CH₂.CH₂.N), 3.9–4.1 [together 6H, m, N.CH₂.CH₂.N, NCH₃ (s at 3.97 discerneable) and high-field half of 3-CH₂S Abq], 4.23 (1H, J 14 Hz, low-field half of 3-CH₂S ABq), 5.23 and 5.25 (together 1H, each s, 6-H, minor and major rotamer respectively), 5.93 and 5.95 (together 1H, each s, NH.CH.CO, minor and major rotamer respectively), 7.47 (2H, s, aromatics), and 8.13 and 8.46 (together 1H, each s, NH.CH.O, major and minor rotamer respectively).

MIC (μg/ml) against P. Mirabilis 889 is 0.06.

EXAMPLE 16

(a) 2-(4,5-Dihydroxy-2-fluorophenyl)-N-(2,3-dioxo-4-ethylpiperazin-1-ylcarbonyl)glycine 4-Fluorocatechol (3.06 g., 24 mmole) was added to a suspension of N-(2,3-dioxo-4-ethylpiperazin-1-ylcarbonyl)-2-hydroxyglycine (3.89 g, 15 mmole) in glacial acetic acid (13.5 ml) and concentrated sulphuric acid (1.5 ml). The mixture was stirred overnight, diluted with water (50 ml), adjusted to pH6 with saturated sodium carbonate and washed with ethyl acetate (2×50 ml). The aqueous solution was acidified to pH 2.5 and extracted with ethyl acetate (5×40 ml). The combined extracts were dried and evaporated to give the crude product, 6.10 g, as a foam.

(b) 2-(4,5-Diacetoxy-2-fluorophenyl)-N-(2,3-dioxo-4-ethylpiperazin-1-ylcarbonyl)glycine Acetic anhydride (3.3 ml) was added to a solution of 2-(4,5-dihydroxy-2-fluorophenyl)-N-(2,3-dioxo-4-ethylpiperazin-1-ylcarbonyl)glycine (6.10), triethylamine (6.9 ml) and 4-dimethylaminopyridine (0.1 g) in dichloromethane (50 ml). The solution was stirred for two hours then washed with 5N hydrochloric acid (20 ml) and water (2×50 ml), dried and evaporated to a foam, 6.19 g. The product crystallised from acetone, 1.65 g, mp 177°–179°, δ[(CD₃)₂CO+(CD₃)₂SO] 1.13 (3H, t, J 7 H, CH₂CH₃), 2.25 (6H, s, 2×OCOCH₃), 3.45 (2H, q, J 7 Hz, CH₂CH₃), 3.5–4.2 (4H, m, 2×NCH₂), 4.3–4.7 (1H, broad, CO₂H), 5.65 (1H, d, J 7 Hz, CH NH), 7.13 (1H, d, J$_{FH}$ 8 Hz, Ar 3-H), 7.28 (1H, d, J$_{FH}$ 5 Hz, Ar 6-H), 9.75 (1H, J 7 Hz, CHNH).

(c) Benzyl 6β-[D-2-(4,5-diacetoxy-2-fluorophenyl-2-(2,3-dioxo-4-ethylpiperazin-1-ylcarbonylamino)acetamido]-6α-formamidopenicillanate Oxalyl chloride (0.4 ml) and DMF (4 μl) were added to D,L-2-(4,5-diacetoxy-2-fluorophenyl)-N-(2,3-dioxo-4-ethylpiperazin-1-ylcarbonyl)glycine (0.906 g, 2 mmole) in dichloromethane (20 ml). The mixture was stirred for 1.5 hours and the resulting solution evaporated to give the acid chloride as a foam. This in dichloromethane (10 ml) was added dropwise to benzyl 6,β-amino-6α-formamidopenicillanate (0.738 g, 2.4 mmole) and pyridine (0.2 ml) in dichloromethane (20 ml) cooled in an ice bath. The reaction was stirred for 30 minutes then washed with 1N hydrochloric acid (25 ml), water (25 ml), 1N sodium bicarbonate solution (25 ml) and water (25 ml), dried and evaporated to a foam which was chromatographed on silica gel eluting with 20% cyclohexane in methyl acetate to give benzyl 6,β-[L-2-

(4,5-diacetoxy-2-fluorophenyl)-2-(2,3-dioxo-4-ethylpiperazin-1-ylcarbonylamino)acetamido]-6,α-formamidopenicillanate, 0.30 g, followed by the title compound, 0.56 g, 36%, δ[(CD$_3$)$_2$CO] 1.07, 1.24 (6H, 2×s, 2×2CH$_3$), 1.17 (3H, t, J 7 Hz, NCH$_2$CH$_3$), 2.26, 2.27 (6H, 2×s, 2×OCOCH$_3$), 3.49 (2H, q, J 7 Hz, NCH$_2$CH$_3$), 3.6–4.1 (4H, m, NCH$_2$CH$_2$N), 4.43 (1H, s, 3H), 5.20 (2H, s, OCH$_2$) 5.59 (1H, s, 5H), 5.96 (1H, d, J 7 Hz, CHNH), 7.15 (1H, d, J$_{FH}$ 10 Hz, Ar 3H), 7.2–7.6 (6H, m, Ph, Ar 6H), 8.18 (1H, s, CHO), 8.26 (1H, s, CONH), 8.85 (1H, s, CONH) 10.6 (1H, d, J 7 Hz, CHNH).

(d) Sodium 6β-[D-2-(4,5-diacetoxy-2-fluorophenyl)-2-(2,3-dioxo-4-ethylpiperazin-1-ylcarbonylamino)acetamido]-6α-formamidopenicillanate Benzyl 6,β-[D-2-(4,5-diacetoxy-2-fluorophenyl)-2-(2,3-dioxo-4-ethylpiperazin-1-ylcarbonylamino)acetamido]-6,α-formamidopenicillanate (0.55 g) in THF (15 ml) was hydrogenated in the presence of 10% palladium on carbon (0.5 g) for 30 minutes. The mixture was filtered, the filtrate evaporated to dryness and the residue (0.49 g) dissolved in acetone (10 ml). To this was added 1.85N sodium 2-ethylhexanoate in 4-methylpentan-2-one (0.38 ml) and the precipitated sodium salt collected, washed with acetone and ether and dried in vacuo, 0.42 g, 83%, identical with the material described in example 8c.

(e) Sodium 6,β-[D-2-(4,5-dihydroxy-2-fluorophenyl)-2-(2,3-dioxo-4-ethylpiperazin-1-ylcarbonylamino)acetamido]-6,α-formamidopenicillanate Sodium 6,β-[D-2-(4,5-diacetoxy-2-fluorophenyl)-2-(2,3-dioxo-4-ethylpiperazin-1-ylcarbonylamino)acetamido]-6,α-formamidopenicillanate (0.40 g) in water (5 ml) was adjusted to pH8 with saturated sodium carbonate solution, anhydrous sodium sulphite (0.2 g), added and pH 8.25±0.25 maintained for 50 minutes. The reaction solution was chromatographed on HP20SS eluting with water then 2% THF in water. The fractions containing the product were combined and freeze dried to provide the title compound, 0.23 g, 64%. ν$_{max}$ (KBr) 1772, 1715, 1676, 1609, 1506 and 1193 cm$^{-1}$, δ(D$_2$O) 0.92, 1.30 (6H, 2×s, 2×2CH$_3$), 1.18 (3H, t, J 7 Hz, NCH$_2$CH$_3$), 3.49 (2H, q, J 7 Hz, NCH$_2$CH$_3$), 3.68, 3.98 (4H, 2×m, NCH$_2$CH$_2$N), 4.18 (1H, s, 3H), 5.55, 5.59 (2H, 2×s, 5H, CHNH), 6.67 (1H, d, J$_{FH}$ 11.4 Hz, Ar 3H), 6.90 (1H, d, J$_{FH}$ 7 Hz, Ar 6H), 8.11 (1H, s, CHO). MIC against Proteus mirabilis 889 0.25 μg/ml.

EXAMPLE 17

7β[D-2-(4,5-Diacetoxy-2-fluorophenyl)-2-[(4-ethyl-2,3-dioxopiperazin-1-yl)carbonylamino]acetamido]-7α-formamidocephalosporanate, sodium salt (a) t-Butyl 7β-[D-2-(4,5-diacetoxy-2-fluorophenyl)-2-[(4-ethyl-2,3-dioxopiperazin-1-yl)carbonylamino]acetamido]-7α-formamidocephalosporanate Freshly prepared 2-(4,5-diacetoxy-2-fluorophenyl)[(4-ethyl-2,3-dioxopiperazin-1-yl)carbonylamino]-acetyl chloride, generated by treatment of the corresponding acid (109 mg, 0.199 mmol) with oxalyl chloride (50.5 mg, 0.397 mmol) in dry dichloromethane (4 ml) and N,N-dimethylformamide (1/5 drop) for 90 min, was taken up in dry dichloromethane (2 ml) and added to a stirred solution of t-butyl 7β-amino-7α-formamidocephalosporanate (65 mg, 0.175 mmol) in dry dichloromethane (3 ml), followed by pyridine (14 mg, 0.175 mmol). After 30 mins the mixture was diluted with dichloromethane and washed successively with dilute aqueous sodium hydrogen carbonate, dilute hydrochloric acid, and saturated brine, dried (MgSO$_4$), and evaporated. The residue was chromatographed on silica gel to give the title compound (45 mg); ν$_{max}$ (CHCl$_3$) 2380, 2990, 1780, 1760, 1740, 1720, and 1690 cm$^{-1}$, δ(CDCl$_3$) 1.25 (3H, t, J 7 Hz, N.CH$_2$.CH$_3$), 1.56 (9H, s, CMe$_3$), 2.10 (3H, s, CH$_2$OCOCH$_3$), 2.29 (6H, s, 2×OCOCH$_3$), 2.99 and 3.32 (together 2H, ABq, J 17 Hz, 2-CH$_2$), 3.45–3.75 [together 4H, m, N.CH$_2$.CH$_2$.N and N.CH$_2$.CH$_3$ [q. (J 7 Hz) at 3.57 discernable]], 3.85–4.20 (2H, m, N.CH$_2$.CH$_2$.N), 4.79 and 5.07 (together 2H, ABq, J 13.5 Hz, 3-CH$_2$OAc), 5.15 (1H, s, 6-H), 5.87 (1H, d, J 6.5 Hz, NH.CH.CO), 7.02 (1H, d, J 9.5 Hz, aromatic 3-H), 7.31 (1H, d, J 7.0 Hz, aromatic 6-H), 7.84 br and 8.13 br (each 1H, s, 2×amide NH), 8.18 (1H, s, NH.CHO, major rotamer), and 10.04 (1H, d, J6.5 Hz, CH.NH.CO.

(b) 7β[D-2-(4,5-Diacetoxy-2-fluorophenyl)-2-[(4-ethyl-2,3-dioxopiperazin-1-yl)carbonylamino]acetamido]-7α-formamidocephalosporanate, sodium salt t-Butyl 7β[D-2-(4,5-diacetoxy-2-fluorophenyl)-2-[(4-ethyl-2,3-dioxopiperazin-1-yl)carbonylamino]acetamido]-7α-formamidocephalosporanate (38 mg) was dissolved in trifluoroacetic acid (2 ml) and after 10 min at room temperature, the solvent removed in vacuo. The residue was taken up in dilute aqueous sodium hydrogen carbonate, pH adjusted to 6.8 and solution chromatographed on Diaion HP20SS. The relevant fractions were lyophilised to afford the title compound (28 mg) as a white solid, ν$_{max}$ (KBr) 3400, 2980, 1770, 1685, 1610, 1500, 1370 and 1205 cm$^{-1}$, δ(D$_2$O) 1.19 (3H, t, J 7 Hz, N.CH$_2$CH$_3$), 2.08 (3H, s, CH$_2$OCOCH$_3$), 2.33 (6H, s, 2×OCOCH$_3$), 3.06 (1H, J 17.5 Hz, high-field half of 2-CH$_2$S ABq), 3.4–3.6 (together 3H, m, N.CH$_2$.CH$_3$ and low-field half of 2-CH$_2$S ABq), 3.6–3.8 and 3.9–4.1 (each 2H, m, N.CH$_2$.CH$_2$.N), 4.6–4.9 (2H, 3-CH$_2$OAc, obscured by solvent), 5.30 (1H, s, 6-H), 5.82 (1H, s, NH.CH.CO), 7.22 (1H, d, J10 Hz, aromatic 3-H), 7.45 (1H, d, J7 Hz, aromatic 6-H) and 8.15 and 8.47 (together 1H, each s, NH.CHO, major and minor rotamer respectively).

MIC (μg/ml) against P. Mirabilis 899 is 0.5

We claim:
1. A compound of the formula (II)

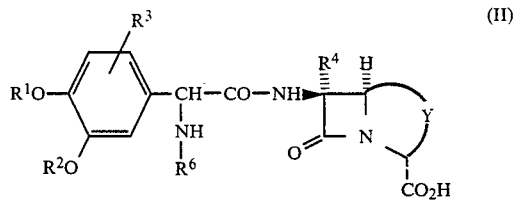

or a pharmaceutically acceptable salt or in vivo hydrolysable ester thereof;
wherein
each of R$^1$ and R$^2$, which may be identical or different, denotes hydrogen or a group selected from the group consisting of those of the formulae —COR$^5$ and —CO—OR$^5$;

R$_3$ denotes a halogen atom;

R$^4$ denotes hydrogen, methoxy, hydroxymethyl, or formamido;

R$^5$ denotes an unsubstituted hydrocarbon group or a hydrocarbon group substituted by one or more substituents selected from the group consisting of: alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and alkyl moieties having from 1 to 6 carbon atoms;

R$^6$ denotes hydrogen or a group selected from the group consisting of those of the formulae —COR$^7$ and ·CO—N(R$^7$)R$^8$;

R$^7$ denotes an unsubstituted hydrocarbon group, an unsubstituted heterocyclic group, a substituted hydrocarbon group, or a substituted heterocyclic group, wherein the substituents for the said hydrocarbon and heterocyclic groups are one or more substituents selected from the group consisting of: alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, alkylcarbonyl, arylthio, arylcarbonyl, arylalkoxy, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted napthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

R$^8$ denotes hydrogen or alkyl having from 1 to 6 carbon atoms;

Y denotes a grouping selected from the group consisting of those of the formulae $$\begin{array}{ccc} -S & -S & \text{and} \quad -Y^1 \\ | & | & | \\ -C(CH_3)_2 & -CH_2 & CH_2 \\ & & | \\ & & =C-Z \end{array}$$

Y$^1$ denotes oxygen, sulphur, or —CH$_2$—;

Z denotes hydrogen, halogen, alkoxy having from 1 to 4 carbon atoms, or a group selected from the group consisting of those of the formulae —CH$_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4, of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;
or said ring being fused to another heterocyclic or carbocyclic ring.

2. A compound of the formula (III):

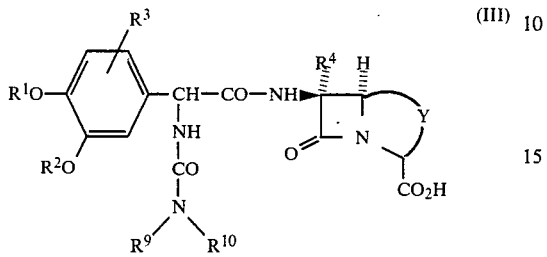

wherein
each of $R^1$ and $R^2$, which may be identical or different, denotes hydrogen or a group selected from the group consisting of those of the formulae $-COR^5$ and $-CO-OR^5$;

$R^3$ denotes a halogen atom;
$R^4$ denotes hydrogen, methoxy, hydroxymethyl, or fomamido;
$R^5$ denotes an unsubstituted hydrocarbon group or a hydrocarbon group substituted by one or more substituents selected from the group consisting of:
alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;
each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;
each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;
each of said alkyl groups and moieties having from 1 to 6 carbon atoms;
$R^9$ denotes hydrogen or alkyl having from 1 to 6 carbon atoms; and
$R^{10}$ denotes a heterocyclyl ring having 5 or 6 ring atoms, one or two of said ring atoms being nitrogen atoms, and said ring being unsubstituted or being substituted or being fused to another heterocyclic or carbocyclic ring; or $R^9$ and $R^{10}$ together with the nitrogen atom to which they are attached denote a heterocyclyl ring as defined for $R^{10}$ above;
wherein the substituents on said heterocyclyl ring $R^{10}$ or $-N(R^9)R^{10}$ are selected from the group consisting of:
alkyl, alkenyl, alkynyl, cycloalkyl, cycloalkenyl, phenyl, oxo, hydroxy, alkoxy, alkenyloxy, cycloalkyloxy, phenoxy, pyrimidyloxy, benzyloxy, mercapto, substituted mercapto, alkylsulphonyl, substituted imino, amino, alkylamino, alkenylamino, cycloalkylamino, phenylamino, and benzylamino;
each of said alkyl groups and moieties having from 1 to 6 carbon atoms;
each of said alkyl and phenyl groups and moieties being unsubstituted or being substituted by one or more substituents selected from the group consisting of alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;
Y denotes a grouping selected from the group consisting of those of the formulae

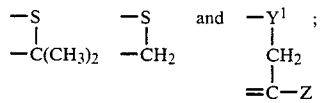

$Y^1$ denotes oxygen, sulphur, or $-CH_2-$;
Z denotes hydrogen, halogen, alkoxy having from 1 to 4 carbon atoms, or a group selected from the group consisting of those of the formulae $-CH_2-Q$ and $-CH=CH-Q$;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, a nitrogen-containing heterocyclyl bonded thru a nitrogen atom of the heterocyclyl group, or a group of the formula $-S-Het$;

said carbon-bonded heterocyclyl group containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;
said nitrogen-bonded heterocyclyl group containing from one to four hetero-atoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and napthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen, and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

3. A compound of the formula (IV):

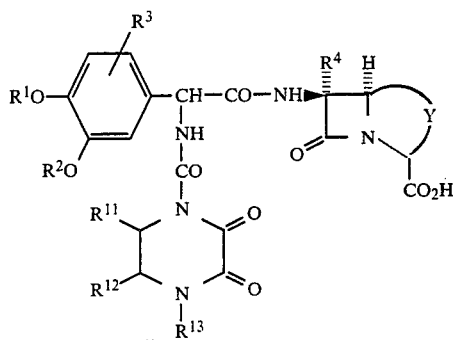

wherein each of $R^1$ and $R^2$, which may be identical or different, denotes hydrogen or a group selected from the group consisting of those of the formulae —$COR^5$ and —CO—$OR^5$;

$R^3$ denotes a halogen atom;

$R^4$ denotes hydrogen, methoxy, hydroxymethyl, or formamido;

$R^5$ denotes an unsubstituted hydrocarbon group or a hydrocarbon group substituted by one or more substituents selected from alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

each of $R^{11}$ and $R^{12}$, which may be the same or different, denotes hydrogen, alkyl, substituted alkyl, halogen, carboxy, hydroxy, amino, or alkoxy; or $R^{11}$ and $R^{12}$ together denote a carbocyclic or heterocyclic ring fused to the pyrazine ring and having five or six ring atoms;

$R^{13}$ denotes hydrogen, alkyl, substituted alkyl, aryl or aralkyl;

wherein each of said alkyl groups and moieties $R^{11}$, $R^{12}$ and $R^{13}$ has from 1 to 6 carbon atoms;

wherein the substituents of each of said substituted alkyl groups $R^{11}$, $R^{12}$ and $R^{13}$ are selected from the group consisting of amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl; and wherein each of said aryl groups and moieties $R^{13}$ is selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

Y denotes a grouping selected from the group consisting of those of the formulae

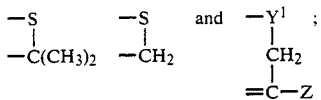

$Y^1$ denotes oxygen, sulphur, or —$CH_2$—;

Z denotes hydrogen, halogen, alkoxy having from 1 to 4 carbon atoms, or a group selected from the group consisting of those of the formulae —$CH_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four hetero-atoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

4. A compound according to claim 1 wherein $R^3$ denotes chlorine.

5. A compound according to claim 2, wherein $R^3$ denotes chlorine.

6. A compound according to claim 3, wherein $R^3$ denotes chlorine.

7. A compound according to claim 1, wherein Y denotes —S—$CH_2$—C(Z)= wherein Z denotes hydrogen, halogen, alkoxy having from 1 to 4 carbon atoms, or a group selected from the group consisting of those of the formulae —$CH_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

8. A compound according to claim 4, wherein Y denotes —S—$CH_2$—C(Z)= wherein Z denotes hydrogen, halogen, alkoxy having from 1 to 4 carbon atoms, or a group selected from the group consisting of those of the formulae —$CH_2$—Q and —CH=CH—Q;

substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

9. A compound according to claim 3, wherein Y denotes —S—$CH_2$—C(Z)=.

10. A compound selected from the group consisting of sodium 6,β-[D,L-2-(2-chloro-4,5-dihydroxyphenyl)-2-(2,3-dioxo-4-ethylpiperazin-1-ylcarbonylamino)acetamido penicillanate;

sodium 6,β[D,L-2-(2-chloro-4,5-diacetoxyphenyl)-2-(2,3-dioxo-4-ethylpiperazin-1-ylcarbonylamino)acetamido]bisnorpenicillanate;

6,β-[D,L-2-amino-2-(2-chloro-4,5-diacetoxyphenyl)acetamido]penicillanic acid;

sodium 6,β-[D,L-2-(2-chloro-4,5-diacetoxyphenyl)-2-(2,3-dioxo-4-ethylpiperazin-1-ylcarbonylamino)acetamido]-6,α-methoxypenicillanate;

sodium 6,6² -[D,L-2-(2-chloro-4,5-diacetoxyphenyl)-2-2,3-dioxo-4-ethylpiperazin-1-ylcarbonylamino)acetamido]-6,α-formamidopenicillanate;

sodium 6,β-[D-2-(2-chloro-4,5-diacetoxyphenyl)-2-(2,3-dioxo-4-ethylpiperazin-1-ylcarbonylamino acetamido]-6,α-formamidopenicillanate;

sodium 6,β-[D,L-2-(4,5-diacetoxy-2-fluorophenyl)-2-(2,3-dioxo-4-ethylpiperazin-1-ylcarbonylamino)acetamido]penicillanate;

sodium 6,β-[D-2-(4,5-diacetoxy-2-fluorophenyl)-2-(2,3-dioxo-4-ethylpiperazin-1-ylcarbonylamino)acetamido]-6,α-formamidopenicillanate;

sodium 6,β-[D-2-(2-chloro-4,5-diacetoxyphenyl)-2-(2,3-dioxo-4-ethyl-piperazin-1-ylcarbonylamino)acetamido]-penicillanate;

sodium 6,β-[D,L-2-(bromo-4,5-diacetoxyphenyl)-2-(2,3-dioxo-4-ethylpiperazin-1-ylcarbonylamino)acetamido]-penicillanate;

sodium 6,β-[D-2-(4,5-dihydroxy-2-fluorophenyl)-2-(2,3-dioxo-4-ethylpiperazin-1-ylcarbonylamino)acetamido]-penicillanate;

sodium 6,β-[D-2-(2-chloro-4,5-dihydroxyphenyl)-2-(2,3-dioxo-4-ethyl-piperazin-1-ylcarbonylamino)acetamido]-6,α-formamidopenicillanate 7β[D-2-(2-bromo-4,5-diacetoxyphenyl)-2-[(4-ethyl-2,3-dioxopiperazin-1-yl)carbonylamino]acetamido]-7α-formamidocephalosporanate, sodium salt;

7β[D-2-(2-chloro-4,5-diacetoxyphenyl)-2-[4-ethyl-2,3-dioxopiperazin-1-yl)carbonylamino]acetamido]-7α-formamidocephalosporanate, sodium salt;

7β-[D-2-(2-chloro-4,5-diacetoxyphenyl-2-[(4-ethyl-2,3-dioxopiperazin-1-yl)carbonylamino]acetamido]-7α-formamido-3[(1-methyl-1H-tetrazol-5-yl)thiomethyl]ceph-3-em-4-carboxylic acid, sodium salt;

sodium 6,-β-[D-2-(2-fluoro-4,5-dihydroxyphenyl)-2-(2,3-dioxo-4-ethyl-piperazin-1-ylcarbonylamino)acetamido]-6,α-formamidopenicillanate; and 7β-[D-2-(2-fluoro-4,5-diacetoxyphenyl)-2-[4-(ethyl-2,3-dioxoperazin-1-yl)carbonylamino]acetamido]-7α-formamido cephalosporanate, sodium salt.

11. A compound of the formula (X):

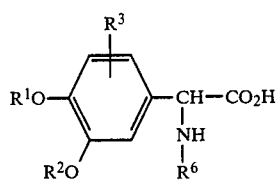

(X)

wherein each of R¹ and R², which may be identical or different, denotes hydrogen or a group selected from the group consisting of those of the formulae —COR⁵ and —CO—OR⁵;

R³ denotes a halogen atom;

R⁵ denotes an unsubstituted hydrocarbon group or a hydrocarbon group substituted by one or more substituents selected from the group consisting of alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said hetero-cyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

R⁶ denotes hydrogen or a group selected from the group consisting of those of the formulae —COR⁷ and —CO—N(R⁷)R⁸;

R⁷ denotes an unsubstituted hydrocarbon group, an unsubstituted heterocyclic group, a substituted hydrocarbon group, or a substituted heterocyclic group, wherein the substituents for the said hydrocarbon and heterocyclic groups are one or more substituents selected from the group consisting of: alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, alkylcarbonyl, arylthio, arylcarbonyl, arylalkoxy, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

$R^8$ denotes hydrogen or alkyl having from 1 to 6 carbon atoms.

12. A pharmaceutical composition useful for treating bacterial infections in humans and animals which comprises an antibacterially effective amount of a compound of the formula (II):

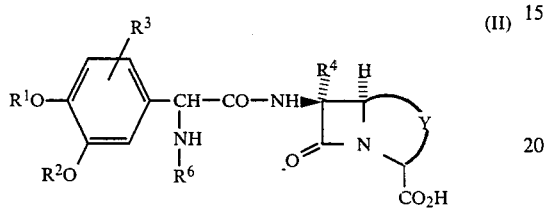

wherein
each of $R^1$ and $R^2$, which may be identical or different, denotes hydrogen or a group selected from the group consisting of those of the formulae —$COR^5$ and —CO—$OR^5$;

$R_3$ denotes a halogen atom;

$R^4$ denotes hydrogen, methoxy, hydroxymethyl, or formamido;

$R^5$ denotes an unsubstituted hydrocarbon group or a hydrocarbon group substituted by one or more substituents selected from the group consisting of alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

$R^6$ denotes hydrogen or a group selected from the group consisting of those of the formulae —$COR^7$ and —CO—N($R^7$)$R^8$;

$R^7$ denotes an unsubstituted hydrocarbon group, an unsubstituted heterocyclic group, a substituted hydrocarbon group, or a substituted heterocyclic group, wherein the substituents for the said hydrocarbon and heterocyclic groups are one or more substituents selected from the group consisting of alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, alkylcarbonyl, arylthio, arylcarbonyl, arylalkoxy, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

$R^8$ denotes hydrogen or alkyl having from 1 to 6 carbon atoms;

Y denotes a grouping selected from the group consisting of those of the formulae

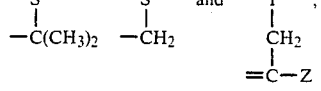

$Y^1$ denotes oxygen, sulphur, or —$CH_2$—;

Z denotes hydrogen, halogen, alkoxy having from 1 to 4 carbon atoms, or a group selected from the group consisting of those of the formulae —$CH_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and alkyl moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5 or 6 ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring, in combination with a pharmaceutically acceptable carrier.

13. A method of treating bacterial infections in humans and animals which comprises administering to a human or animal in need thereof an antibacterially effective amount of a compound of the formula (II):

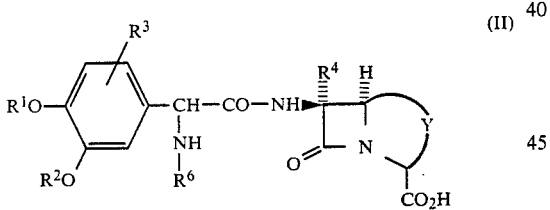

or a pharmaceutically acceptable salt or in vivo hydrolysable ester thereof;
wherein
each of $R^1$ and $R^2$, which may be identical or different, denotes hydrogen or a group selected from the group consisting of those of the formulae —$COR^5$ and —$CO$—$OR^5$;

$R_3$ denotes a halogen atom;
$R^4$ denotes hydrogen, methoxy, hydroxymethyl, or formamido;
$R^5$ denotes an unsubstituted hydrocarbon group or a hydrocarbon group substituted by one or more substituents selected from the group consisting of:
alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and alkyl moieties having from 1 to 6 carbon atoms;

$R^6$ denotes hydrogen or a group selected from the group consisting of those of the formulae —$COR^7$ and —$CO$—$N(R^7)R^8$;

$R^7$ denotes an unsubstituted hydrocarbon group, an unsubstituted heterocyclic group, a substituted hydrocarbon group, or a substituted heterocyclic group, wherein the substituents for the said hydrocarbon and heterocyclic groups are one or more substituents selected from the group consisting of:
alkyl, amino, alkanoylamino, monoalkylamino, dialkylamino, hydroxy, alkoxy, mercapto, alkylthio, sulphamoyl, carbamoyl, amidino, guanidino, niro, chloro, bromo, fluoro, carboxy, carboxy salts, carboxy esters, alkanoyloxy, alkylcarbonyl, arylthio, arylcarbonyl, arylalkoxy, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, substituted phenyl, and substituted naphthyl, wherein the substituents for said substituted phenyl and naphthyl are from one to five substituents selected from the group consisting of halogen, alkyl phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

$R^8$ denotes hydrogen or alkyl having from 1 to 6 carbon atoms;

Y denotes a grouping selected from the group consisting of those of the formulae

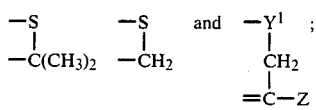

Y$^1$ denotes oxygen, sulphur, or —CH$_2$—;

Z denotes hydrogen, halogen, alkoxy having from 1 to 4 carbon atoms, or a group selected from the group consisting of those of the formulae —CH$_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygem and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring, in combination with a pharmaceutically acceptable carrier.

14. A pharmaceutical composition useful for treating bacterial infections in humans and animals which comprises an antibacterially effective amount of a compound of the formula (III):

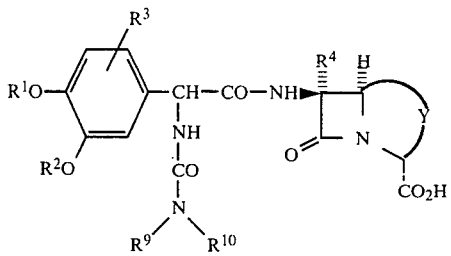

wherein
each of R$^1$ and R$^2$, which may be identical or different, denotes hydrogen or a group selected from the group consisting of those of the formulae —COR$^5$ and —CO—OR$^5$;

R$^3$ denotes a halogen atom;

R$^4$ denotes hydrogen, methoxy, hydroxymethyl, or fomamido;

R$^5$ denotes an unsubstituted hydrocarbon group or a hydrocarbon group substituted by one or more substituents selected from the group consisting of: alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

R$^9$ denotes hydrogen or alkyl having from 1 to 6 carbon atoms; and

R$^{10}$ denotes a heterocyclyl ring having 5 or 6 ring atoms, one or two of said ring atoms being nitrogen atoms, and said ring being unsubstituted or being substituted or being fused to another heterocyclic or carbocyclic ring; or R$^9$ and R$^{10}$ together with the nitrogen atom to which they are attached denote a heterocyclyl ring as defined for R$^{10}$ above;

wherein the substituents on said heterocyclyl ring R$^{10}$ or —N(R$^9$)R$^{10}$ are selected from the group consisting of:

alkyl, alkenyl, alkynyl, cycloalkyl, cycloalkenyl, phenyl, oxo, hydroxy, alkoxy, alkenyloxy, cycloalkyloxy, phenoxy, pyrimidyloxy, benzyloxy, mercapto, substituted mercapto, alkylsulphonyl, substituted imino, amino, alkylamino, alkenylamino, cycloalkylamino, phenylamino, and benzylamino;

each of said alkyl groups and moieties having from 1 to 6 carbon atoms;

each of said alkyl and phenyl groups and moieties being unsubstituted or being substituted by one or more substituents selected from the group consisting of alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy, carboxy salts, carboxy esters, alkanoyloxy, arylthio, alkylcarbonyl, heterocyclyl, heterocyclylthio, and heterocyclylcarbonyl;

Y denotes a grouping selected from the group consisting of those of the formulae

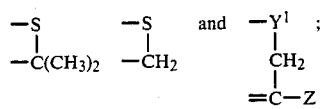

$Y^1$ denotes oxygen, sulphur, or —CH$_2$—;

Z denotes hydrogen, halogen, alkoxy having from 1 to 4 carbon atoms, or a group selected from the group consisting of those of the formulae —CH$_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, a nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four hetero-atoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen, and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring, in combination with a pharmaceutically acceptable carrier.

15. A pharmaceutical composition useful for treating bacterial infections in humans and animals which comprises an antibacterially effective amount of a compound of the formula (IV):

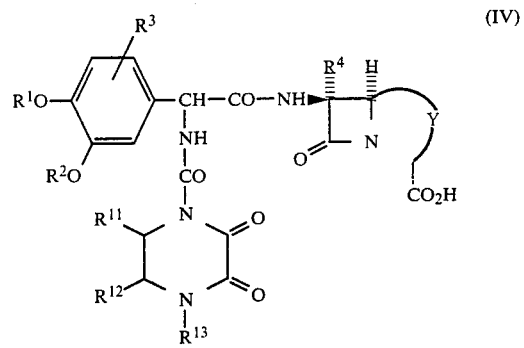

wherein each of $R^1$ and $R^2$, which may be identical or different, denotes hyrogen or a group selected from the group consisting of those of the formulae —COR$^5$ and —CO—OR$^5$;

$R^3$ denotes a halogen atom;

$R^4$ denotes hydrogen, methoxy, hydroxymethyl, or formamido;

$R^5$ denotes an unsubstituted hydrocarbon group or a hydrocarbon group substituted by one or more substituents selected from alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of aid aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

each of $R^{11}$ and $R^{12}$, which may be the same or different, denotes hydrogen, alkyl, substituted alkyl, halogen, carboxy, hydroxy, amino, or alkoxy; or $R^{11}$ and $R^{12}$ together denote a carbocyclic or heterocyclic ring fused to the pyrazine ring and having five or six ring atoms;

$R^{13}$ denotes hydrogen, alkyl, substituted alkyl, aryl or aralkyl;

wherein each of said alkyl groups and moieties $R^{11}$, $R^{12}$ and $R^{13}$ has from 1 to 6 carbon atoms;

wherein the substituents of each of said substituted alkyl groups $R^{11}$, $R^{12}$ and $R^{13}$ are selected from the group consisting of amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl; and wherein each of said aryl groups and moieties $R^{13}$ is selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

Y denotes a grouping selected from the group consisting of those of the formulae

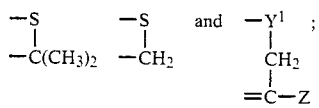

$Y^1$ denotes oxygen, sulphur, or —CH$_2$—;

Z denotes hydrogen, halogen, alkoxy having from 1 to 4 carbon atoms, or a group selected from the group consisting of those of the formulae

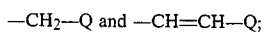

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula

said carbon-bonded heterocyclyl group containing from one to four hetero-atoms selected from oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four hetero-atoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring, in combination with a pharmaceutically acceptable carrier.

16. A composition according to claim 12 wherein $R^3$ denotes chlorine.

17. A composition according to claim 14, wherein $R^3$ denotes chlorine.

18. A composition according to claim 15, wherein $R^3$ denotes chlorine.

19. A composition according to claim 12, wherein Y denotes —S—CH$_2$—C(Z)= wherein Z denotes hydrogen, halogen, alkoxy having from 1 to 4 carbon atoms, or a group selected from the group consisting of those of the formulae

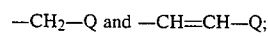

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

20. A composition according to claim 14, wherein Y denotes —S—CH$_2$—C(Z)=wherein Z denotes hydrogen, halogen, alkoxy having from 1 to 4 carbon atoms, or a group selected from the group consisting of those of the formulae —CH$_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

21. A composition according to claim 15 wherein Y is —S—CH$_2$—C(Z)=wherein

Z is hydrogen, halogen, alkoxy of 1 to 4 carbon atoms, or a group selected from the group consisting of those of the formulae:

—CH$_2$Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and alkyl moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5 or 6 ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

22. A pharmaceutical composition useful for treating bacterial infections in humans and animals which comprises an antibacterially effective amount of:

sodium 6,$\beta$-[D,L-2-(2-chloro-4,5-dihydroxyphenyl)-2-(2,3-dioxo-4-ethylpiperazin-1-ylcarbonylamino)acetamido penicillanate;

sodium 6,$\beta$[D,L-2-(2-chloro-4,5-diacetoxyphenyl)-2-(2,3-dioxo-4-ethylpiperazin-1-ylcarbonylamino)acetamido]bisnorpenicillanate;

6,$\beta$-[D,L-2-amino-2-(2-chloro-4,5-diacetoxyphenyl)acetamido]penicillanic acid;

sodium 6,$\beta$-[D,L-2-(2-chloro-4,5-diacetoxyphenyl)-2-(2,3-dioxo-4-ethylpiperazin-1-ylcarbonylamino)acetamido]-6,$\alpha$-methoxypenicillanate;

sodium 6,$\beta$-[D,L-2-(2-chloro-4,5-diacetoxyphenyl)-2-2,3-dioxo-4-ethylpiperazin-1-ylcarbonylamino)acetamido]-6,$\alpha$-formamidopenicillanate;

sodium 6,$\beta$-[D-2-(2-chloro-4,5-diacetoxyphenyl)-2-(2,3-dioxo-4-ethylpiperazin-1-ylcarbonylamino acetamido]-6,$\alpha$-formamidopenicillanate;

sodium 6,$\beta$-[D,L-2-(4,5-diacetoxy-2-fluorophenyl)-2-(2,3-dioxo-4-ethylpiperazin-1-ylcarbonylamino)acetamido]penicillanate;

sodium 6,$\beta$-[D-2-(4,5-diacetoxy-2-fluorophenyl)-2-(2,3-dioxo-4-ethylpiperazin-1-ylcarbonylamino)acetamido]-6,$\alpha$-formamidopenicillanate;

sodium 6,$\beta$-[D-2-(2-chloro-4,5-diacetoxyphenyl)-2-(2,3-dioxo-4-ethyl-piperazin-1-ylcarbonylamino)acetamido]-penicillanate;

sodium 6,$\beta$-[D,L-2-(2-bromo-4,5-diacetoxyphenyl)-2-(2,3-dioxo-4-ethylpiperazin-1-ylcarbonylamino)acetamido]-penicillanate;

sodium 6,$\beta$-[D-2-(4,5-dihydroxy-2-fluorophenyl)-2-(2,3-dioxo-4-ethylpiperazin-1-ylcarbonylamino)acetamido]-penicillanate;

sodium 6,$\beta$-[D-2-(2-chloro-4,5-dihydroxyphenyl)-2-(2,3-dioxo-4-ethyl-piperazin-1-ylcarbonylamino)acetamido]-6,60 -formamidopenicillanate 7$\beta$[D-2-(2-bromo-4,5-diacetoxyphenyl)-2-[(4-ethyl-2,3-dioxopiperazin-1-yl)carbonylamino]acetamido]-7$\alpha$-formamidocephalosporanate, sodium salt;

7$\beta$[D-2-(2-chloro-4,5-diacetoxyphenyl)-2-[4-ethyl-2,3-dioxopiperazin-1-yl)carbonylamino]acetamido]-7$\alpha$-formamidocephalosporanate, sodium salt;

7$\beta$-[D-2-(2-chloro-4,5-diacetoxyphenyl-2-[(4-ethyl-2,3-dioxopiperazin-1-yl)carbonylamino]acetamido]-7$\alpha$-formamido-3-[(1-methyl-1H-tetrazol-5-yl)thiomethyl]ceph-3-em-4-carboxylic acid, sodium salt;

sodium 6,-$\beta$-[D-2-(2-fluoro-4,5-dihydroxyphenyl)-2-(2,3-dioxo-4-ethyl-piperazin-1-ylcarbonylamino)acetamido]-6,$\alpha$-formamidopenicillanate; and 7$\beta$-[D-2-(2-fluoro-4,5-diacetoxyphenyl)-2-[4-(ethyl-2,3-dioxoperazin-1-yl)carbonylamino]acetamido]-7$\alpha$-formamido cephalosporanate, sodium salt.

23. A method of treating bacterial infections in humans and animals which comprises administering to a human or animal in in need thereof an antibacterially effective amount of a compound of the formula (III):

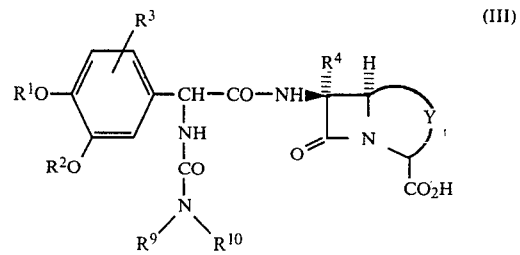

wherein each of $R^1$ and $R^2$, which may be identical or different, denotes hydrogen or a group selected from the group consisting of those of the formulae —$COR^5$ and —CO—$OR^5$;

$R^3$ denotes a halogen atom;

$R^4$ denotes hydrogen, methoxy, hydroxymethyl, or fomamido;

$R^5$ denotes an unsubstituted hydrocarbon group or a hydrocarbon group substituted by one or more substituents selected from the group consisting of: alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

$R^9$ denotes hydrogen or alkyl having from 1 to 6 carbon atoms; and $R^{10}$ denotes a heterocyclyl ring having 5 or 6 ring atoms, one or two of said ring atoms being nitrogen atoms, and said ring being unsubstituted or being substituted or being fused to another heterocyclic or carbocyclic ring; or $R^9$ and $R^{10}$ together with the nitrogen atom to which they are attached denote a heterocyclyl ring as defined for $R^{10}$ above;

wherein the substituents on said heterocyclyl ring $R^{10}$ or $-N(R^9)R^{10}$ are selected from the group consisting of:

alkyl, alkenyl, alkynyl, cycloalkyl, cycloalkenyl, phenyl, oxo, hydroxy, alkoxy, alkenyloxy, cycloalkyloxy, phenoxy, pyrimidyloxy, benzyloxy, mercapto, substituted mercapto, alkylsulphonyl, substituted imino, amino, alkylamino, alkenylamino, cycloalkylamino, phenylamino, and benzylamino;

each of said alkyl groups and moieties having from 1 to 6 carbon atoms;

each of said alkyl and phenyl groups and moieties being unsubstituted or being substituted by one or more substituents selected from the group consisting of alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

Y denotes a grouping selected from the group consisting of those of the formulae

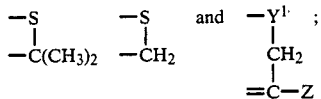

$Y^1$ denotes oxygen, sulphur, or $-CH_2-$;

Z denotes hydrogen, halogen, alkoxy having from 1 to 4 carbon atoms, or a group selected from the group consisting of those of the formulae $-CH_2-Q$ and $-CH=CH-Q$;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, a nitrogen-containing heterocyclyl bonded thru a nitrogen atom of the heterocyclyl group, or a group of the formula $-S-Het$;

said carbon-bonded heterocyclyl group containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four hetero-atoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen, and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring; in combination with a pharmaceutically acceptable carrier.

24. A method of treating bacterial infections in humans and animals which comprises administering to a human or animal in need thereof an antibacterially effective amount of a compound of the formula (IV):

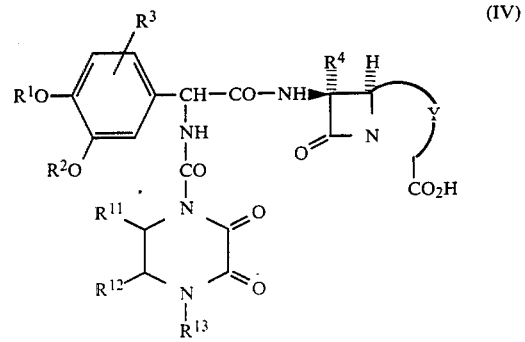

wherein each of $R^1$ and $R^2$, which may be identical or different, denotes hydrogen or a group selected from the group consisting of those of the formulae $-COR^5$ and $-CO-OR^5$;

$R^3$ denotes a halogen atom;

$R^4$ denotes hydrogen, methoxy, hydroxymethyl, or formamido;

$R^5$ denotes an unsubstituted hydrocarbon group or a hydrocarbon group substituted by one or more substituents selected from alkyl, amino, alkanoylamino, monoalkylamino, dialkylamino, hydroxy, alkoxy, mercapto, alkylthio, sulphamoyl, carbamoyl, amidino, guanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl;

each of said heterocyclyl groups and moieties containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

each of said aryl groups and moieties being selected from the group consisting of unsubstituted phenyl, unsubstituted naphthyl, substituted phenyl, and substituted naphthyl, wherein the substituents for said substituted phenyl and napthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

each of $R^{11}$ and $R^{12}$, which may be the same or different, denotes hydrogen, alkyl, substituted alkyl, halogen, carboxy, hydroxy, amino, or alkoxy; or $R^{11}$ and $R^{12}$ together denote a carbocyclic or heterocyclic ring fused to the pyrazine ring and having five or six ring atoms;

$R^{13}$ denotes hydrogen, alkyl, substituted alkyl, aryl or aralkyl;

wherein each of said alkyl groups and moieties $R^{11}$, $R^{12}$ and $R^{13}$ has from 1 to 6 carbon atoms;

wherein the substituents of each of said substituted alkyl groups $R^{11}$, $R^{12}$ and $R^{13}$ are selected from the group consisting of amino, alkanoylamino, monoalkylamino, dialkylamino, hydroxy, alkoxy, mercapto, alkylthio, sulphamoyl, carbamoyl, amidino, quanidino, nitro, chloro, bromo, fluoro, carboxy, carboxy salts, carboxy esters, alkanoyloxy, arylthio, arylcarbonyl, heterocyclyl, heterocyclylthio, and heterocyclylcarbonyl; and wherein each of said aryl groups and moieties $R^{13}$ is selected from the group consisting of unsubstituted phenyl, unsubstituted naphthyl, substituted phenyl, and substituted naphthyl, wherein the substituents for said substituted phenyl and naphtyl are from one to five substituents selected from the group consisting of phenyl, alkoxy, haloalkyl, hydroxy, amino, nitro, carboxy, alkoxycarbonyl, alkoxycarbonylalkyl, alkylcarbonyloxy and alkylcarbonyl;

Y denotes a grouping selected from the group consisting of those of the formulae

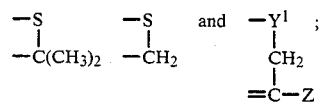

$Y^1$ denotes oxygen, sulphur, or —$CH_2$—;

Z denotes hydrogen, halogen, alkoxy having from 1 to 4 carbon atoms, or a group selected from the group consisting of those of the formulae —$CH_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from oxygen, nitrogen and sulphur, and being unsubstituted or being substituted by one from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four hetero-atoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, caroxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring; in combination with a pharmaceutically acceptable carrier.

25. A method according to claim 13 wherein $R^3$ is chlorine.

26. A method according to claim 23 wherein $R^3$ is chlorine.

27. A method according to claim 24 wherein $R^3$ is chlorine.

28. A method according to claim 13, wherein Y denotes —S—$CH_2$—C(Z)=
wherein
Z denotes hydrogen, halogen, alkoxy having from 1 to 4 carbon atoms, or a group selected from the group consisting of those of the formulae —$CH_2$—Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of substituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from said 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

29. The method according to claim 23 wherein Y denotes —S—CH$_2$—C(Z)= wherein

Z denotes hydrogen, halogen, alkoxy having from 1 to 4 carbon atoms, or a group selected from the group consisting of those of the formulae —CH$_2$—Q and —CH=CH—Q;

Q denotes hydrogen, halogen, hydroxy, mercapto, cyano, carboxy, carbamoyloxy, carboxylic acid, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from the group consisting of alkyl, alkoxy, hydroxyalkyl, alkenyl, alkoxyalkyl, carboxyalkyl, alkylsulphonyl, sulphonylalkyl, carbamoylmethyl, carbamoyl, trifluoromethyl, hydroxy, halogen, oxo, dialkylaminoalkyl, and aminoalkyl;

each of said aryl groups and moieties being selected from the group consisting of unsubstituted phenyl, unsubstituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5- or 6-ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

30. A method according to claim 24 wherein Y is —S—CH$_2$—C(Z)= wherein

Z is hydrogen, halogen, alkoxy of 1 to 4 carbon atoms, or a group selected from the group consisting of those the formulae:

—CH$_2$Q and —CH=CH—Q;

Q denotes hydrogen, halogen, hydroxy, mercapto, cyano, carboxy, carbamoyloxy, carboxylic ester, alkoxy having from 1 to 4 carbon atoms, acyloxy, aryl, heterocyclyl bonded thru a carbon atom of the heterocyclyl group, nitrogen-containing heterocyclyl bonded thru a nitrogen atom of the heterocyclyl group, or a group of the formula —S—Het;

said carbon-bonded heterocyclyl group containing from one to four hetero-atoms selected from the group consisting of oxygen, nitrogen and sulphur, and being unsubstituted or being substituted by from one to three substituents selected from the group consisting of halogen, alkyl, alkoxy, haloalkyl, hydroxy, amino, carboxy, alkoxycarbonyl, alkoxycarbonylalkyl, aryl and oxo;

said nitrogen-bonded heterocyclyl group containing from one to four heteroatoms selected from the group consisting of nitrogen, oxygen and sulphur, and being unsubstituted or substituted by one or two substituents selected from alkyl, alkoxy, hydroxyalkyl, alkenyl, alkoxyalkyl, carboxyalkyl, alkylsulphonyl, sulphnylalkyl, carbamoylmethyl, carbamoyl, trifluoromethyl, hydroxy, halogen, oxo, dialkylaminoalkyl, and aminoalkyl;

each of said aryl groups and alkyl moieties being selected from the group consisting of unsubstituted phenyl, unsubstituted naphthyl, substituted phenyl, and substituted naphthyl, wherein the substituents for said substituted phenyl and naphthyl are from one to five substituents selected from the group consisting of halogen, alkyl, phenyl, alkoxy, haloalkyl, hydroxy, amino, nitro, carboxy, alkoxycarbonyl, alkoxycarbonylalkyl, alkylcarbonyloxy and alkylcarbonyl;

each of said alkyl groups and moieties having from 1 to 6 carbon atoms;

Het denotes a heterocyclyl ring having 5 or 6 ring atoms, from 1 to 4 of said ring atoms being selected from the group consisting of nitrogen, oxygen and sulphur, and said ring being unsubstituted or substituted by one or two substituents selected from the group consisting of:

alkyl, alkoxy, hydroxyalkyl, alkenyl, alkoxyalkyl, carboxyalkyl, sulphonylalkyl, carbamoylalkyl, trifluoromethyl, hydroxy, halogen, oxo, aminoalkyl, substituted-aminoalkyl, and alkylsulphonic acid;

or said ring being fused to another heterocyclic or carbocyclic ring.

31. A method according to claim 23 wheren the compound is selected from the group consisting of:

sodium 6,β-[D,L-2-(2-chloro-4,5-dihydroxyphenyl)-2-(2,3dioxo-4-ethylpiperazin-1-ylcarbonylamino)acetamido penicillanate;

sodium 6,β[D,L-2-(2-chloro-4,5-diacetoxyphenyl)-2-(2,3-dioxo-4-ethylpiperazin-1-ylcarbonylamino)acetamido]bisnorpenicillanate;

6,β-[D,L-2-amino-2-(2-chloro-4,5-diacetoxyphenyl)acetamido]penicillanic acid;

sodium 6,β-[D,L-2-(2-chloro-4,5-diacetoxyphenyl)-2-(2,3-dioxo-4-ethylpiperazin-1-ylcarbonylamino)acetamido]-6,α-methoxypenicillanate;

sodium 6β-[D,L-2-(2-chloro-4,5-diacetoxyphenyl)-2-2,3-dioxo-4-ethylpiperazin-1-ylcarbonylamino)acetamido]-6,α-formamidophenicillanate;

sodium 6,β-[D-2-(2-chloro-4,5-diacetoxyphenyl)-2-(2,3-dioxo-4-ethylpiperazin-1-ylcarbonylaminoacetamido]-6,α-formamidopenicillanate;

sodium 6,β-[D,L-2-(4,5-diacetoxy-2-fluorophenyl)-2-(2,3-dioxo-4-ethylpiperazin-1-ylcarbonylamino)acetamido]penicillanate;

sodium 6,β-[D-2-(4,5-diacetoxy-2-fluorophenyl)-2-(2,3-dioxo-4-ethylpiperazin-1-ylcarbonylamino)acetamido]-6,α-formamidopenicillanate;

sodium 6,β-[D-2-(2-chloro-4,5-diacetoxyphenyl)-2-(2,3-dioxo-4-ethyl-piperazin-1-ylcarbonylamino)acetamido]-penicillanate;

sodium 6,β-[D,L-2-(2-bromo-4,5-diacetoxyphenyl)-2-(2,3-dioxo-4-ethylpiperazin-1-ylcarbonylamino)acetamido]-penicillanate;

sodium 6,β-[D-2-(4,5-dihydroxy-2-fluorophenyl)-2-(2,3-dioxo-4-ethylpiperazin-1-ylcarbonylamino)acetamido]-penicillanate;

sodium 6,β-[D-2-(2-chloro-4,5-dihydroxyphenyl)-2-(2,3-dioxo-4-ethyl-piperazin-1-ylcarbonylamino)acetamido]-6,α-formamidopenicillanate 7β[D-2-(2-bromo-4,5-diacetoxyphenyl)-2-[(4-ethyl-2,3-dioxopiperazin-1-yl)carbonylamino]acetamido]-7α-formamidocephalosporonate, sodium salt;

7β[D-2-(2-chloro-4,5diacetoxyphenyl)-2-[4-ethyl-2,3-dioxopiperazin-1-yl)carbonylamino]acetamido]-7α-formamidocephalosporonate, sodium salt;

7β-[D-2-(2-chloro-4,5-diacetoxyphenyl-2-[(4-ethyl-2,3-dioxopiperazin-1-yl)carbonylamino]acetamido]-7α-formamido-3[(1-methyl-1H-tetrazol-5-yl)thiomethyl]ceph-3-em-4-carboxylic acid, sodium salt;

sodium 6,-β-[D-2-(2-fluoro-4,5-dihydroxyphenyl)-2-(2,3-dioxo-4-ethyl-piperazin-1-ylcarbonylamino)acetamido]-6,α-formamidopenicillanate; and 7β-[D-2-(2-fluoro-4,5-diacetoxyphenyl)-2-[4-(ethyl-2,3-dioxoperazin-1-yl)carbonylamino]acetamido]-7α-formamidocephalosporonate, sodium salt.

* * * * *